United States Patent
Latimer et al.

(10) Patent No.: US 9,757,133 B2
(45) Date of Patent: Sep. 12, 2017

(54) METHODS AND DEVICES FOR PERFORMING A SURGICAL ANASTOMOSIS

(71) Applicant: Covidien LP, Mansfield, MA (US)

(72) Inventors: Cassandra Latimer, Thornton, CO (US); Arlen Ward, Thornton, CO (US)

(73) Assignee: Covidien LP, Mansfield, MA (US)

( * ) Notice: Subject to any disclaimer, the term of this patent is extended or adjusted under 35 U.S.C. 154(b) by 290 days.

(21) Appl. No.: 14/326,764

(22) Filed: Jul. 9, 2014

(65) Prior Publication Data

US 2016/0007999 A1 Jan. 14, 2016

(51) Int. Cl.
| | |
|---|---|
| *A61B 17/68* | (2006.01) |
| *A61B 90/30* | (2016.01) |
| *A61B 17/064* | (2006.01) |
| *A61B 17/115* | (2006.01) |
| *A61B 17/10* | (2006.01) |
| *A61B 17/11* | (2006.01) |
| *A61B 90/00* | (2016.01) |

(52) U.S. Cl.
CPC ........ *A61B 17/1155* (2013.01); *A61B 17/064* (2013.01); *A61B 17/105* (2013.01); *A61B 17/1114* (2013.01); *A61B 90/30* (2016.02); *A61B 2090/0811* (2016.02)

(58) Field of Classification Search
CPC . A61B 17/068; A61B 17/1155; A61B 17/115; A61B 2017/00022; A61B 90/30; A61B 90/361; A61B 2090/309; A61B 1/06
USPC .......................... 227/175.1, 176.1; 606/219
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |

(Continued)

FOREIGN PATENT DOCUMENTS

| | | |
|---|---|---|
| CA | 908529 A | 8/1972 |
| DE | 1057729 B | 5/1959 |

(Continued)

OTHER PUBLICATIONS

European Search Report EP15175837 dated Nov. 9, 2015.
European Office Action dated Mar. 16, 2017 issued in corresponding EP Application No. 15175837.2.

*Primary Examiner* — Michelle Lopez

(57) ABSTRACT

A circular stapler is disclosed. The circular stapler includes a handle assembly, an elongate body, a cartridge assembly, a trocar, and a light source. The elongate body extends from the handle assembly and defines a longitudinal axis. The cartridge assembly is disposed adjacent a distal end of the elongate body and includes a pusher assembly. The pusher assembly is movable to cause staples to be ejected from the cartridge assembly. The trocar is disposed in mechanical cooperation with the cartridge assembly and is longitudinally advanceable to puncture tissue. The light source is disposed in mechanical cooperation with the trocar, and is configured to project a light beam distally of the trocar.

13 Claims, 28 Drawing Sheets

(56) References Cited

U.S. PATENT DOCUMENTS

| | | |
|---|---|---|
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A * | 5/1994 | Welch ............... A61B 17/0218 128/898 |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 * | 1/2002 | Toledano ............. A61B 17/115 227/175.1 |
| 6,343,731 B1 | 2/2002 | Adams et al. |
| 6,387,105 B1 | 5/2002 | Gifford, III et al. |
| 6,398,795 B1 | 6/2002 | McAlister et al. |

(56) References Cited

U.S. PATENT DOCUMENTS

| | | |
|---|---|---|
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |

(56) References Cited

U.S. PATENT DOCUMENTS

| | | |
|---|---|---|
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |

(56) References Cited

U.S. PATENT DOCUMENTS

| | | |
|---|---|---|
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2387943 A2 | 11/2011 |
| EP | 2524656 A2 | 11/2012 |
| EP | 2727549 A1 | 5/2014 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9804196 A1 | 2/1998 |
| WO | 01/54594 A1 | 8/2001 |
| WO | 2008/107918 A1 | 9/2008 |
| WO | 2010045533 A1 | 4/2010 |

* cited by examiner

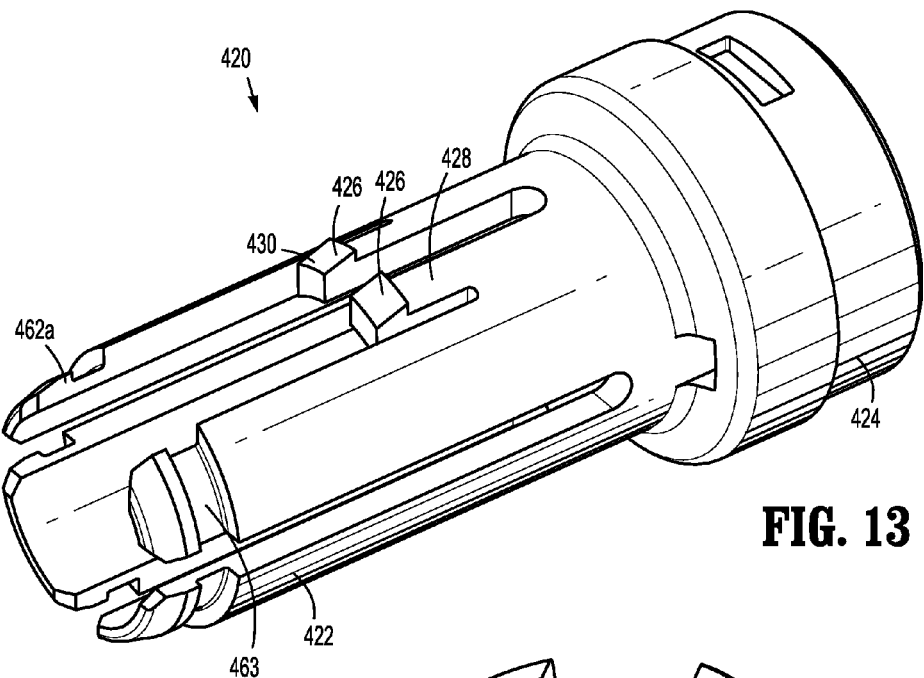
FIG. 13
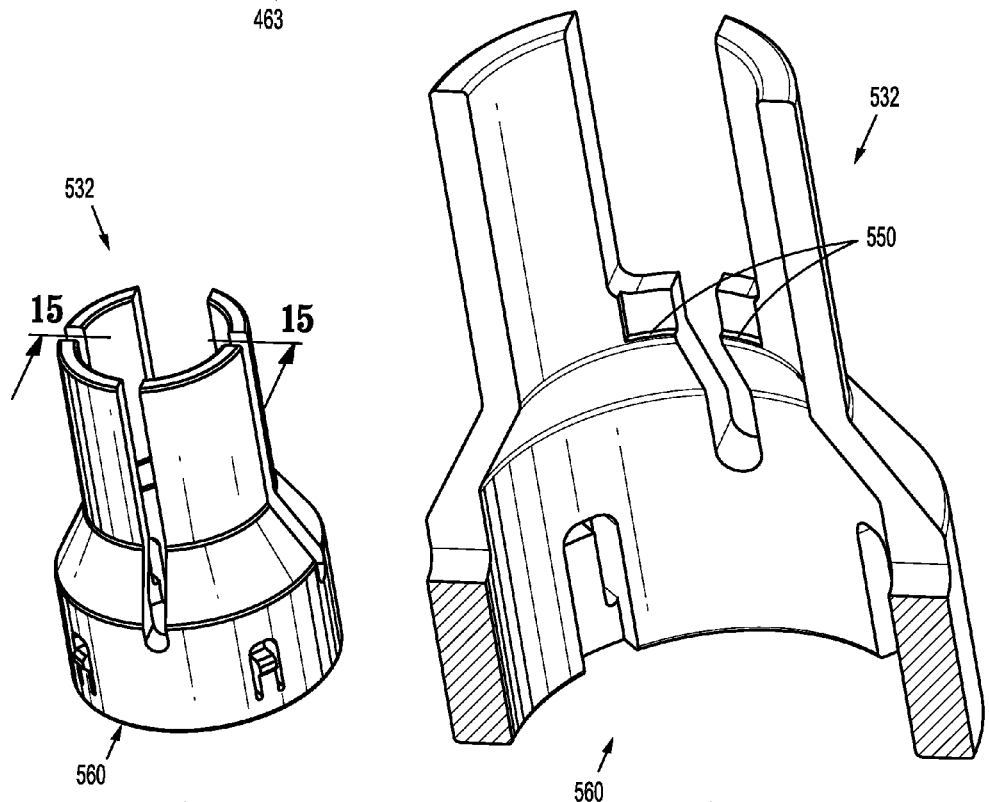
FIG. 14  FIG. 15

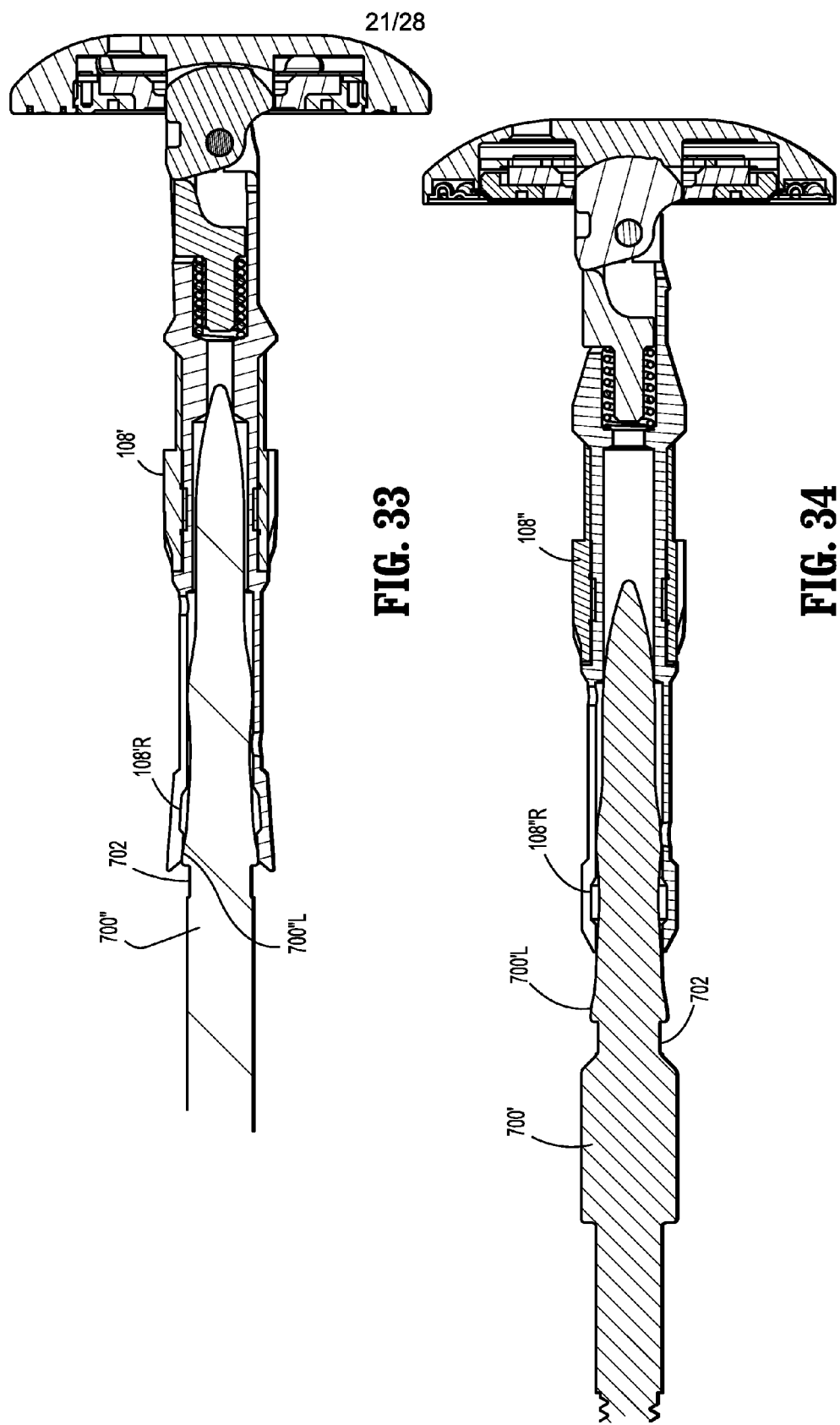

METHODS AND DEVICES FOR PERFORMING A SURGICAL ANASTOMOSIS

BACKGROUND

1. Technical Field

The present disclosure relates generally to a surgical stapling device for applying surgical staples to body tissue. More particularly, the present disclosure relates to a surgical stapling device suitable for performing circular anastomosis and/or treatment to internal walls of hollow tissue organs.

2. Background of Related Art

Anastomosis is the surgical joining of separate hollow organ sections. Typically, an anastomosis procedure follows surgery in which a diseased or defective section of hollow tissue is removed, and the end sections are stapled via a linear surgical stapler. Depending on the desired anastomosis procedure, the end sections may be joined by either circular, end-to-end, or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is advanced to core tissue within the hollow organ to free a tubular passage within the organ. Generally, both the actuation of the staple forming mechanism and the advancement of the knife occur at the same time, i.e., simultaneously.

Besides anastomosis of hollow organs, surgical stapling devices for performing circular anastomosis have been used to treat internal hemorrhoids in the rectum. Typically, during use of a circular stapling device for hemorrhoid treatment, the anvil head and the staple holding component of the surgical stapling device are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling device is fired to remove the hemorrhoidal tissue and staple the cut tissue.

SUMMARY

The present disclosure relates to a circular stapler comprising a handle assembly, an elongate body, a cartridge assembly, a trocar, and a light source. The elongate body extends from the handle assembly and defines a longitudinal axis. The cartridge assembly is disposed adjacent a distal end of the elongate body and includes a pusher assembly. The pusher assembly is movable to cause staples to be ejected from the cartridge assembly. The trocar is disposed in mechanical cooperation with the cartridge assembly and is longitudinally advanceable to puncture tissue. The light source is disposed in mechanical cooperation with the trocar, and is configured to project a light beam distally of the trocar.

In disclosed embodiments, the light source includes a laser. Here, it is disclosed that the laser is at least partially disposed within the trocar. In such embodiments, it is disclosed that a distal tip of the trocar is one of transparent or translucent.

The present disclosure also includes a light source as being least partially disposed within the trocar. Here, it is disclosed that a distal tip of the trocar is also one of transparent or translucent.

In disclosed embodiments, the light source is configured to project a light beam in a concentrated area directly in the path of travel of the trocar. It is further disclosed that the light source is configured to project a light beam that is approximately the size of a diameter of a portion of the trocar that is disposed distally of the cartridge assembly when the trocar is in a longitudinally advanced position.

The present disclosure also relates to a method of performing a surgical procedure. The method includes inserting at least a portion of a circular stapler proximally of a first linear row of staples along a proximal portion of tissue, projecting a light beam from the circular stapler onto the proximal portion of tissue, and advancing a trocar of the circular stapler through the proximal portion of tissue that includes the light beam.

In disclosed embodiments, the method also includes emplacing a first linear row of staples along a proximal portion of tissue prior to inserting at least a portion of the circular stapler proximally of the first linear row of staples. Here, it is disclosed that the method further includes emplacing a second linear row of staples along a distal portion of tissue prior to inserting at least a portion of the circular stapler proximally of the first linear row of staples. It is additionally disclosed that the method includes inserting an anvil assembly of the circular stapler distally of the distal portion of tissue, approximating the anvil assembly and a cartridge assembly of the circular stapler, and joining the proximal portion of tissue with the distal portion of tissue using the circular stapler.

In disclosed embodiments of the method, the light beam is projected from the circular stapler onto a portion of the first linear row of staples. Here, it is disclosed that the trocar is advanced through the portion of the first linear row of staples that includes the light beam.

The presently disclosed method also includes projecting the light beam through a distal tip of the trocar.

DESCRIPTION OF THE DRAWINGS

Embodiments of a surgical stapling instrument are disclosed herein with reference to the drawings, wherein:

FIG. 13 is a perspective view of the knife carrier of FIG. 11;

FIG. 14 is a perspective view of the pusher adapter of FIG. 11;

FIG. 15 is a cut-away perspective view of the pusher adapter taken along line 15-15 in FIG. 14;

FIG. 33 is a longitudinal cross-sectional view the second trocar partially engaged with the first retention rod;

FIG. 34 is a longitudinal cross-sectional view the first trocar partially engaged with the second retention rod;

DETAILED DESCRIPTION

Embodiments of the presently disclosed surgical stapling instrument will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
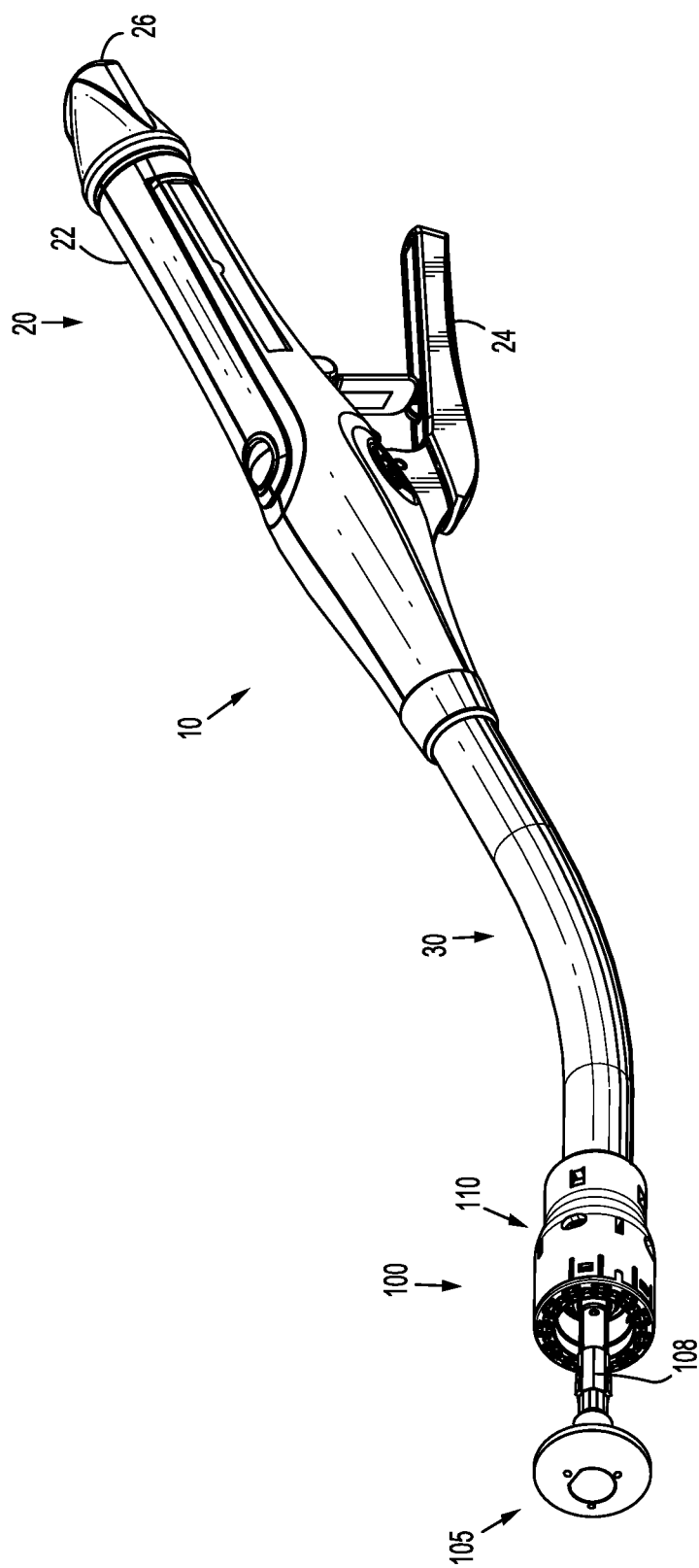
FIG. 1 is a perspective view of a surgical stapling instrument according to embodiments of the present disclosure.

FIG. 1 illustrates an embodiment of a surgical stapling instrument according to the present disclosure, referenced generally as circular stapler 10. Circular stapler 10 includes a handle assembly 20, an elongated body portion 30 extending distally from handle assembly 20, and a shell assembly 100 mounted adjacent a distal end of elongated body portion 30. Handle assembly 20 shown in FIG. 1 is a manually operated handle including a fixed handle 22 and a moveable handle or trigger 24. Handle assembly 20 also includes an approximation knob 26 for moving an anvil assembly 105 relative to a cartridge assembly 110 of shell assembly 100. The structure and function of handle assembly 20 will only be described herein to the extent necessary to fully disclose the operation of shell assembly 100. It is envisioned that shell assembly 100 may be used with any actuation assembly, powered or manual, and capable of two independent actuation strokes, for example. Commonly owned U.S. patent application Ser. No. 12/946,082, filed Nov. 15, 2010, and published as publication no. 2011/0174099 A1, the content of which is incorporated by reference herein in its entirety, discloses a surgical device having a powered actuator assembly including first and second drive members. In addition, it is envisioned that the independent actuation strokes may be completed by the same drive member completing two strokes or by two separate drive members.

It is contemplated that a shell assembly according to the present disclosure can be part of a surgical system. The surgical system can include surgical end effector assemblies (such as shell assembly 100) in various configurations. The elongate shaft of the instrument may itself be a removable and replaceable part of the system. The handle assembly can be manual, powered, or part of a robotic surgical system.

Figure 2:
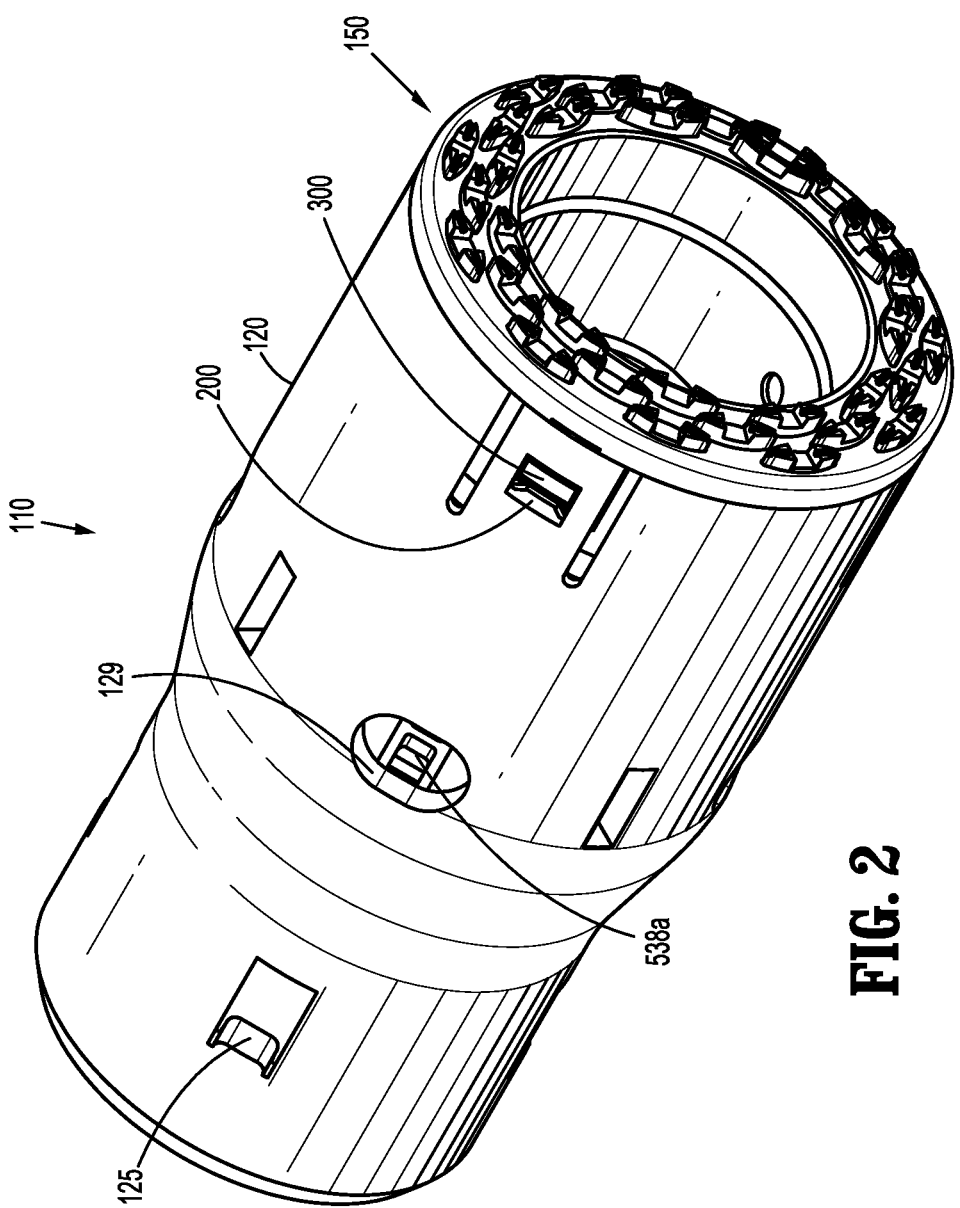
FIG. 2 is an enlarged perspective view of a cartridge assembly of the surgical stapling instrument of FIG. 1.

With reference to FIG. 2, the shell assembly includes a cartridge assembly 110 as shown, and which is operably mounted in the shell assembly. In disclosed embodiments, cartridge assembly 110 is removably secured such that cartridge assembly 110, or a portion thereof, may be replaced and circular stapler 10 may be reused. In other embodiments, only a portion of cartridge assembly 110 is configured to be removed, and subsequently replaced or reloaded. Alternatively, circular stapler 10 may be configured for a single use, i.e., disposable.

Figure 3:
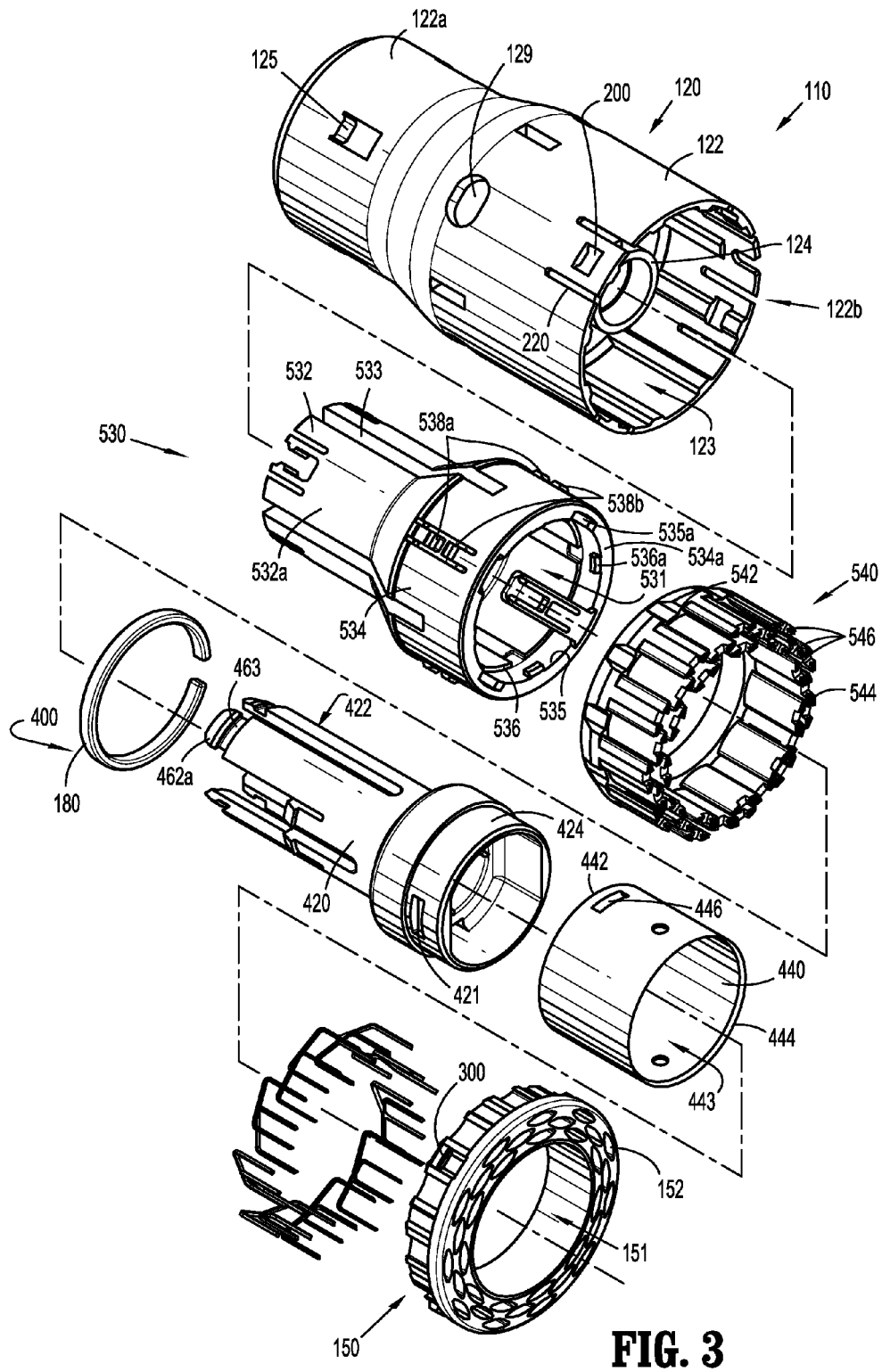
FIG. 3 is an exploded perspective view of the cartridge assembly of FIG. 2.
Figure 4:
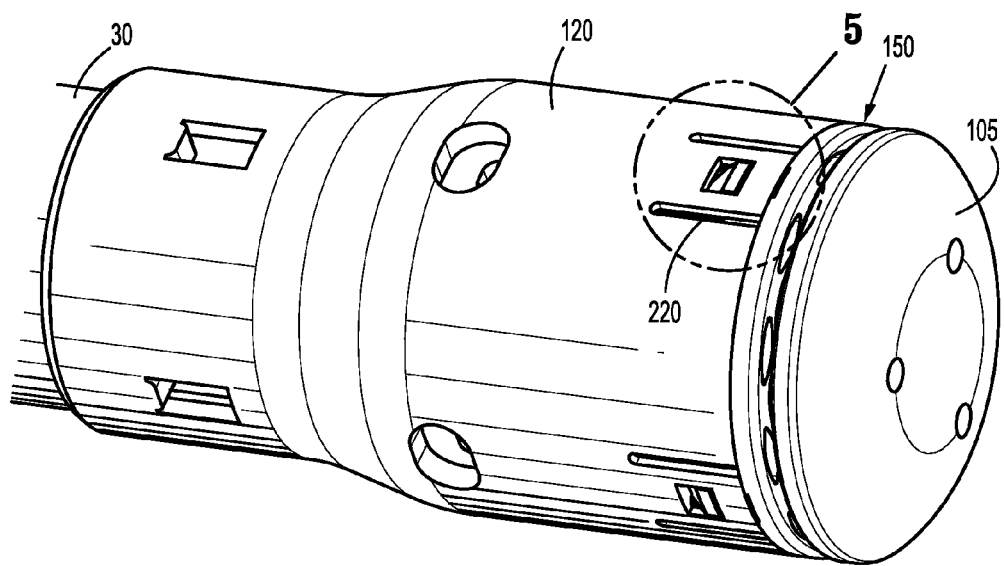
FIG. 4 is a perspective view of a shell assembly in an approximated position, and includes the cartridge assembly of FIGS. 2 and 3.
Figure 5:
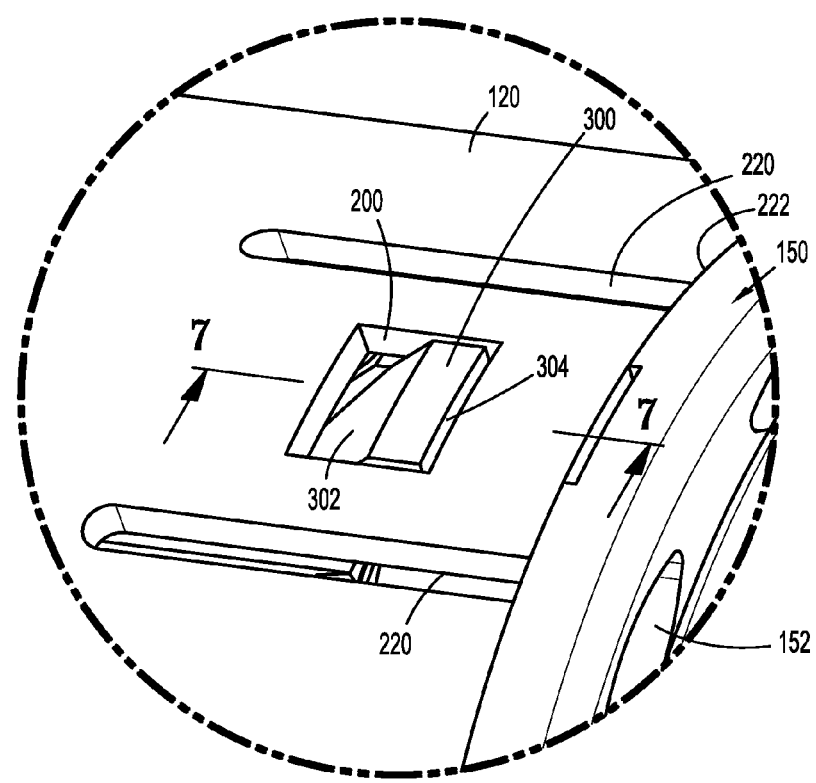
FIG. 5 is an enlarged view of the area of detail indicated in FIG. 4.
Figure 6:
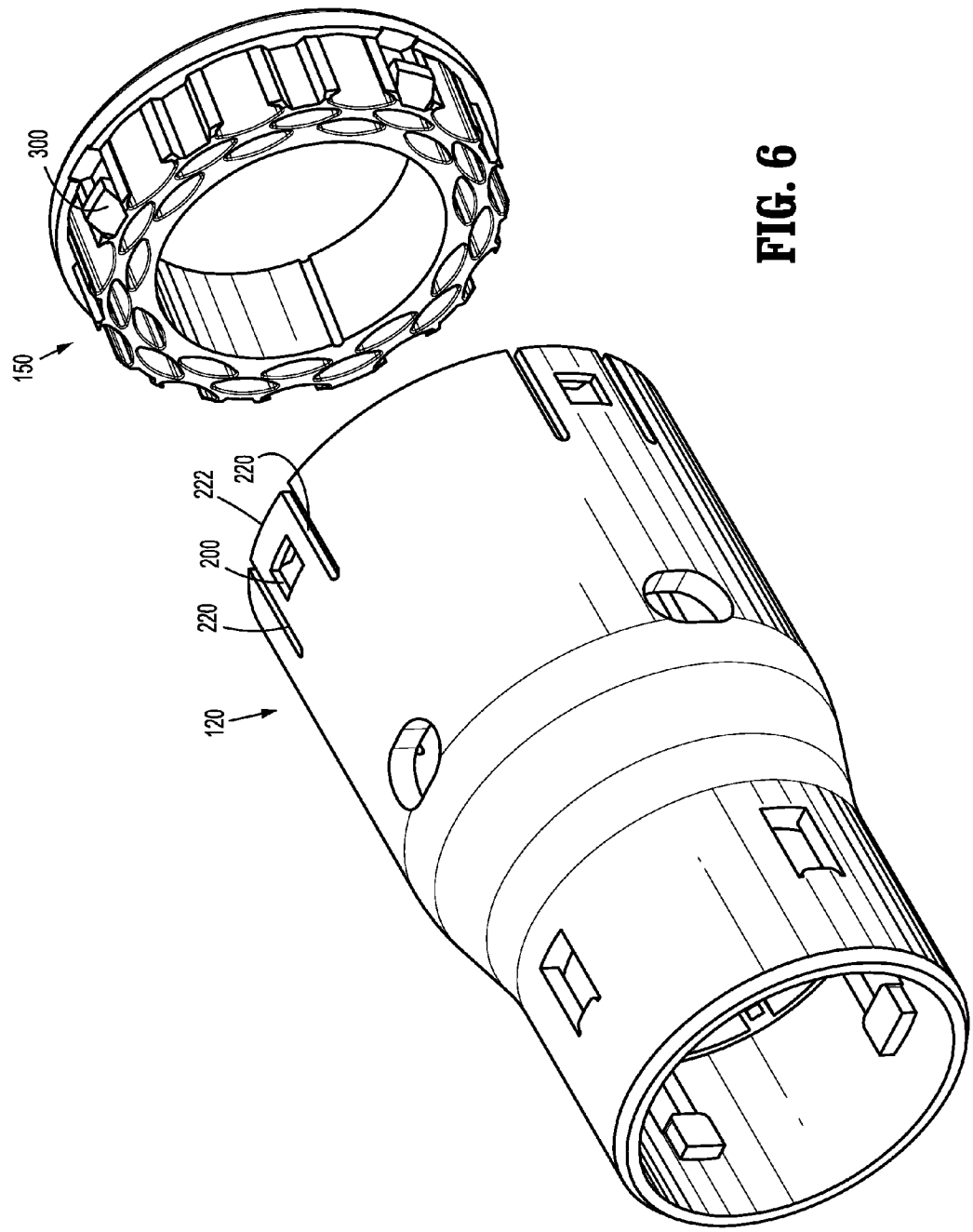
FIG. 6 is a perspective view of a staple guide separated from an outer housing of the cartridge assembly.
Figure 7:
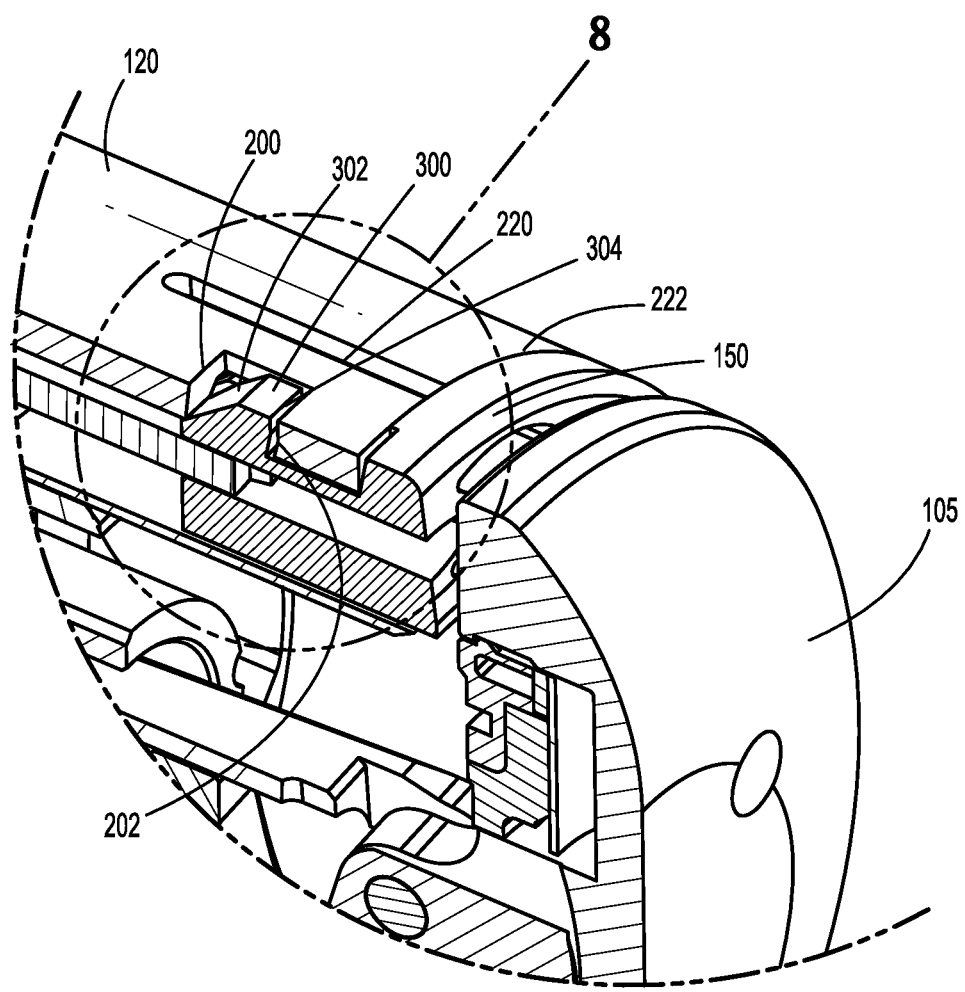
FIG. 7 is a cut-away view of the area of detail indicated in FIG. 5.

With reference to FIGS. 2 and 3, cartridge assembly 110 includes a housing 120, a pusher assembly 530, a staple cartridge 150, and a knife assembly 400. Housing 120 of cartridge assembly 110 includes an outer cylindrical portion 122, an inner cylindrical body 124 and a plurality of radially extending supports or ribs (not shown) extending between and interconnecting inner cylindrical portion 124 and outer cylindrical portion 122. Inner cylindrical portion 124 and outer cylindrical portion 122 are coaxial and define a recess 123 therebetween configured to receive a distal portion of pusher assembly 530 and knife assembly 400.

Knife assembly 400 includes a knife carrier 420 and a circular knife 440. Knife 440 is a substantially cylindrical member having a proximal end 442, a distal end 444, and defines a longitudinal opening 443 therethrough. Knife 440 is sized and configured to be received through recess 123 of staple cartridge 150. Distal end 444 of knife 440 is configured for cutting tissue. Proximal end 442 of knife 440 is configured to be received about a distal portion 424 of knife carrier 420 and includes a pair of opposed tabs 446 configured to be received within respective recesses 421 formed in distal portion 424 of knife carrier 420.

A proximal portion 422 of knife carrier 420 defines an annular groove 463 configured to accommodate snap ring 180 when snap ring 180 is in either a first or compressed condition or in a second or expanded condition. When circular stapler 10 is in the first or initial position, and prior to retraction of pusher adapter 532 following the first stroke of circular stapler 10, snap ring 180 is received completely within annular groove 463 formed in knife carrier 420. Proximal portion 422 of knife carrier 420 further defines a step 462a formed in or adjacent annular groove 463. Step 462a is configured to engage an inner annular portion of snap ring 180 when snap ring 180 is in the second or expanded condition. Further, engagement of snap ring 180 with step 462a prevents radial compression of snap ring 180 during the second or tissue cutting stroke. Further details of snap ring 180 and its engagement with knife carrier 420 are described in U.S. patent application Ser. No. 13/739,246 filed on Jan. 11, 2013, the entire contents of which being incorporated by reference herein.

With continued reference to FIGS. 2 and 3, a proximal end 122a of outer cylindrical portion 122 of housing 120 includes a plurality of tabs 125 formed thereon configured to operably engage cartridge assembly 110 with a distal end of elongated body portion 30 (FIG. 1). Outer cylindrical portion 122 of housing 120 further defines a plurality of openings 129. As will be discussed in further detail below, each of the plurality of openings 129 is configured to engage a pair of a plurality of detents 538a, 538b formed on a distal portion 534 of a pusher adapter 532.

With reference now to FIG. 3, pusher assembly 530 includes pusher adapter 532 and a pusher member 540. Pusher adapter 532 is a substantially cylindrical member having a proximal portion 532a and a distal portion 534. Proximal portion 532a of pusher adapter 532 is configured for operable engagement with a drive member 800 (e.g., see the embodiment disclosed in FIGS. 35-39). Distal portion 534 of pusher adapter 532 is configured to operably engage pusher member 540. As will be discussed in further detail below, pusher member 540 is not securely affixed to pusher adapter 532, such that pusher member 540 remains in an advanced position during the retraction of pusher adapter 532 following the first or stapling stroke of circular stapler 10. In this manner, the force required to move pusher adapter 532 during the second or tissue cutting stroke of circular stapler 10 does not include the force necessary to move pusher member 540.

With continued reference to FIG. 3, pusher adapter 532 defines a longitudinal passage 531 extending therethrough. A distal end of longitudinal passage 531 is sized and configured to receive knife assembly 400 in a sliding manner. Pusher adapter 532 further defines a plurality of longitudinal slots 533 extending along a length thereof. Slots 533 correspond in size and location to the supports (not shown) formed between and interconnecting outer and inner cylindrical portions 122, 124 in housing 120. Pusher adapter 532 is configured to be received within outer cylindrical portion 122 of housing 120 and about inner cylindrical portion 124 of housing 120. In this manner, slots 533 receive the respective supports of housing 120 such that inner cylindrical portion 124 of housing 120 may be received within longitudinal passage 531 of pusher adapter 532. A plurality of recesses 535a are formed in a distal surface 534a of pusher adapter 532 and are configured to engage tabs (not shown) formed on a proximal-facing surface of pusher member 540 (e.g., to ensure radial alignment during the firing stroke). As discussed above, pusher adapter 532 includes a plurality of paired detents 538a, 538b configured to be selectively received within openings 129 formed in outer cylindrical portion 122 of housing 120.

With continued reference to FIG. 3, pusher member 540 includes a proximal portion 542 and a distal portion 544. Proximal portion 542 of pusher member 540 defines a plurality of tabs (not shown) configured to be selectively received within the plurality of recesses 535a formed on distal surface 534a of pusher adapter 532. Distal portion 544 of pusher member 540 includes a plurality of pusher elements 546 extending distally therefrom and arranged in three concentric rows. Pusher elements 546 align with staples "S" received within staple cartridge 150 such that advancement of pusher member 540 relative to staple cartridge 150 causes ejection of staples "S" from staple cartridge 150. A notch 535 formed in distal portion 534 of pusher adapter 532 is configured to receive an outer annular portion of snap ring 180 of knife assembly 400, and a ledge 536 of pusher adapter 532 is configured to engage the outer annular portion of snap ring 180 during the second or cutting stroke of circular stapler 10. Additionally, tabs 536a are configured to retain snap ring 180 in engagement within distal portion 534 of pusher adapter 532.

With reference to FIGS. 2 and 3, staple cartridge 150 is a substantially cylindrical member configured to operably engage distal end 122b of outer cylindrical portion 122 of housing 120 and defines a longitudinal opening 151. Staple cartridge 150 includes a plurality of staple receiving pockets 152 disposed about opening 151 arranged in three concentric rows. Staple receiving pockets 152 align with pusher elements 546 formed on distal portion 544 of pusher member 540.

With reference to FIG. 4-8, the engagement between housing 120 and staple cartridge 150 is illustrated. Housing 120 and staple cartridge 150 are configured to mechanically engage each other prior to use of circular stapler 10 (e.g., during assembly). In this embodiment, housing 120 is engagable with staple cartridge 150 via a mechanical interface. More particularly, housing 120 includes at least one aperture 200 that is engagable with at least one tab 300 on staple cartridge 150.

Figure 8:
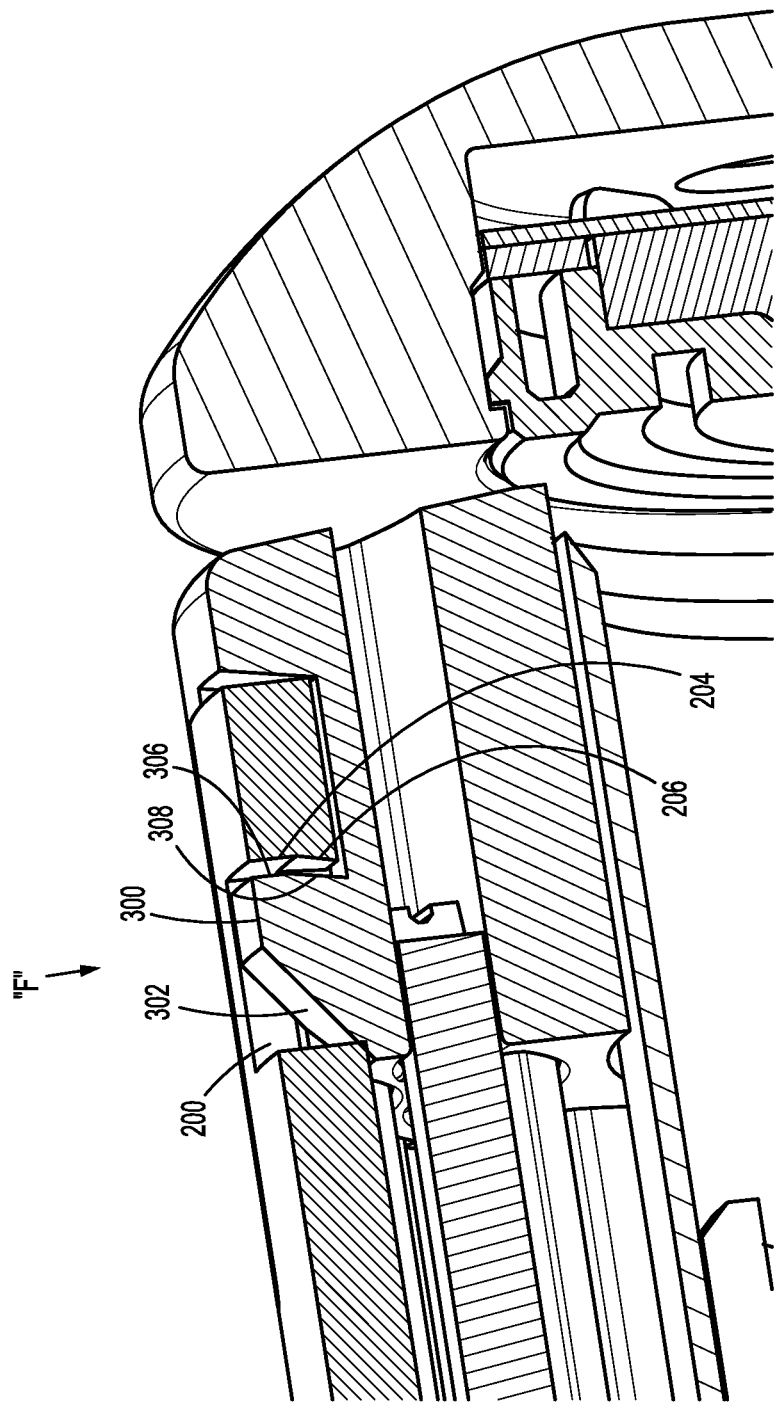
FIG. 8 is an enlarged view of the area of detail indicated in FIG. 7.

Tabs 300 on staple cartridge 150 are inwardly flexible (with respect to a longitudinal axis A-A defined by elongated body portion 30) to facilitate assembly. Tabs 300 include a ramped proximal surface 302, and a distal surface 304 (FIG. 8). It is envisioned that distal surface 304 includes a substantially perpendicular surface 306 (with respect to longitudinal axis A-A), a ramped surface 308, or a combination thereof. In the illustrated embodiment (see FIG. 8, for example), distal surface 304 of tab 300 includes a perpendicular surface 306 and a ramped surface 308. Ramped surface 308 is angled such that the portion closer to the longitudinal axis A-A is disposed proximally of the portion of ramped surface 308 that is farther from the longitudinal axis A-A. It is envisioned that staple cartridge 150 includes any number of tabs 300.

Apertures 200 on housing 120 are dimensioned and positioned for mechanical engagement with tabs 300. It is envisioned that housing 120 includes any number of apertures 200. It is further envisioned that the number of apertures 200 is equal to or unequal to the number of tabs 300. Additionally, it is disclosed that the dimensions and/or orientation of tabs 300 and apertures 200 only allow engagement therebetween in a single radial orientation (e.g., for mistake-proof assembly). It is envisioned that a distal wall 202 of aperture 200 includes a substantially perpendicular surface 204 (with respect to longitudinal axis A-A), a ramped surface 206, or a combination thereof. In the illustrated embodiment (see FIG. 8, for example), distal wall 202 of aperture 200 includes a perpendicular surface 204 and a ramped surface 206. Ramped surface 206 is angled such that the portion closer to the longitudinal axis A-A is disposed proximally of the portion of ramped surface 206 that is farther from the longitudinal axis A-A. As shown, the orientation of distal wall 202 of aperture 200 is complementary to the orientation of distal surface 304 of tab 300.

It is envisioned that the complementary surfaces of distal wall 202 and distal surface 304, including ramped surfaces 206 and 308, respectively, help provide improved retention between housing 120 and staple cartridge 150. In this embodiment, a greater force (e.g., in the substantial direction of arrow "F" in FIG. 8) would be required to disengage staple cartridge 150 from outer housing 120 with respect to an embodiment where distal surface 304 of tab 300 and distal wall 202 of aperture 200 do not include ramped surfaces 308 and 206, respectively.

In the illustrated embodiment, housing 120 also includes a plurality of longitudinal slots 220, with one slot 220 being disposed on each side of each aperture 200. Slots 220 extend proximally from a distal edge 222 of housing 120. It is envisioned that slots 220 enable radially outward flexing of the portion of housing 120 surrounding apertures 200 to facilitate the mechanical engagement between housing 120 and staple cartridge 150. As can be appreciated, to mechanically engage housing 120 and staple cartridge 150, the two components are approximated such that the portion of housing 120 surrounding apertures 200 flexes radially outward to allow tabs 300 of staple cartridge 150 to enter apertures 200. After tabs 300 are within respective apertures 200, the portion of housing 120 surrounding apertures 200 flexes radially inward to effectively lock housing 120 and staple cartridge 150 together.

It is envisioned that the mechanical engagement between housing 120 and staple cartridge 150 is the only type of engagement therebetween. For example, the mechanical engagement eliminates the need for adhesives between the two components or welding the components together.

Figure 9:
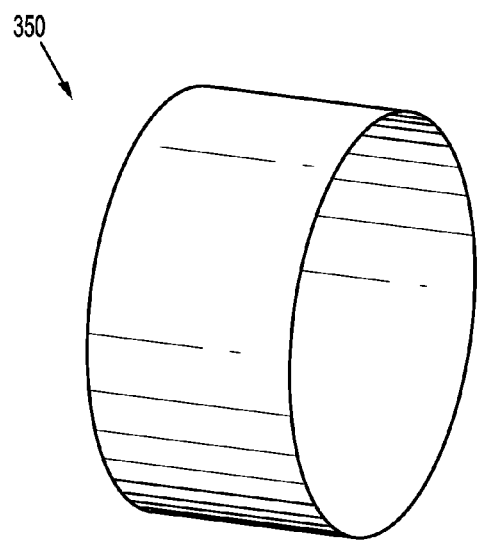
FIG. 9 is a perspective view of a sleeve configured for use with the shell assembly of the present disclosure.
Figure 10:
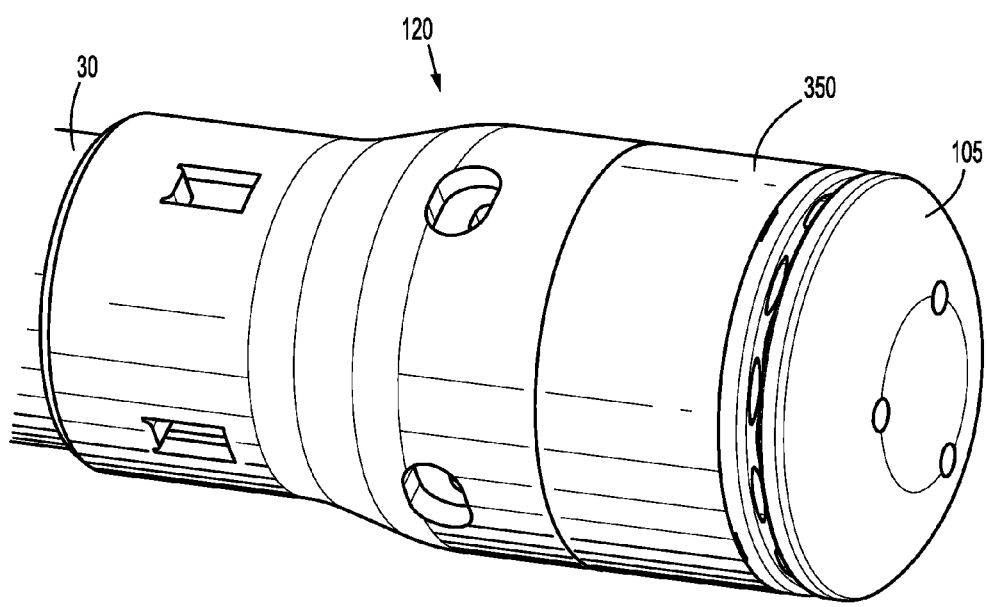
FIG. 10 is a perspective view of the sleeve of FIG. 9 positioned on the shell assembly.
Figure 11:
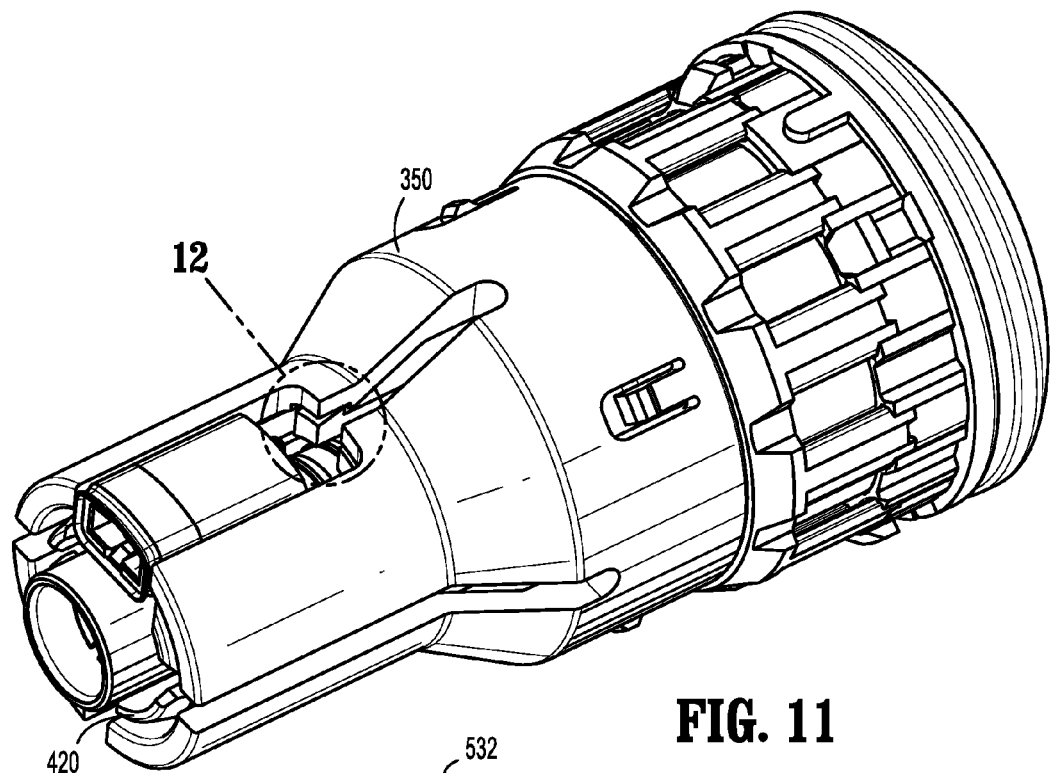
FIG. 11 is a perspective view of a knife carrier engaged with a pusher adapter of the cartridge assembly of the present disclosure.

With reference to FIGS. 9 and 10, the present disclosure includes a label (e.g., an adhesive label) or sleeve (e.g., a shrink sleeve) 350. Sleeve 350 is positionable adjacent a distal portion of housing 120 and is configured to cover apertures 200, slots 220 and tabs 300 (see FIG. 5). The use of sleeve 350 helps ensure tissue does not because trapped or pinched within apertures 200, slots 220 or tabs 300, and also helps limit radially outward movement of tabs 300 with regard to apertures 200 during insertion of housing 120 into tissue, for example.

Additionally, it is envisioned that sleeve 350 can include information (e.g., indicia or a color) relating to lumen and/or staple size of the stapling instrument, for example. It is envisioned that the circumference of sleeve 350 is equal to or larger than the circumference of the distal portion of housing 120. In the embodiments where sleeve 350 has a larger circumference, an overlapping portion of sleeve 350 will cover the longitudinal seam between sleeve 350 and housing 120. It is envisioned that sleeve 350 is made from plastic (e.g., polyvinyl chloride (PVC), polyethylene terephthalate (PET), polypropylene, etc.) or another suitable material.

Figure 12:
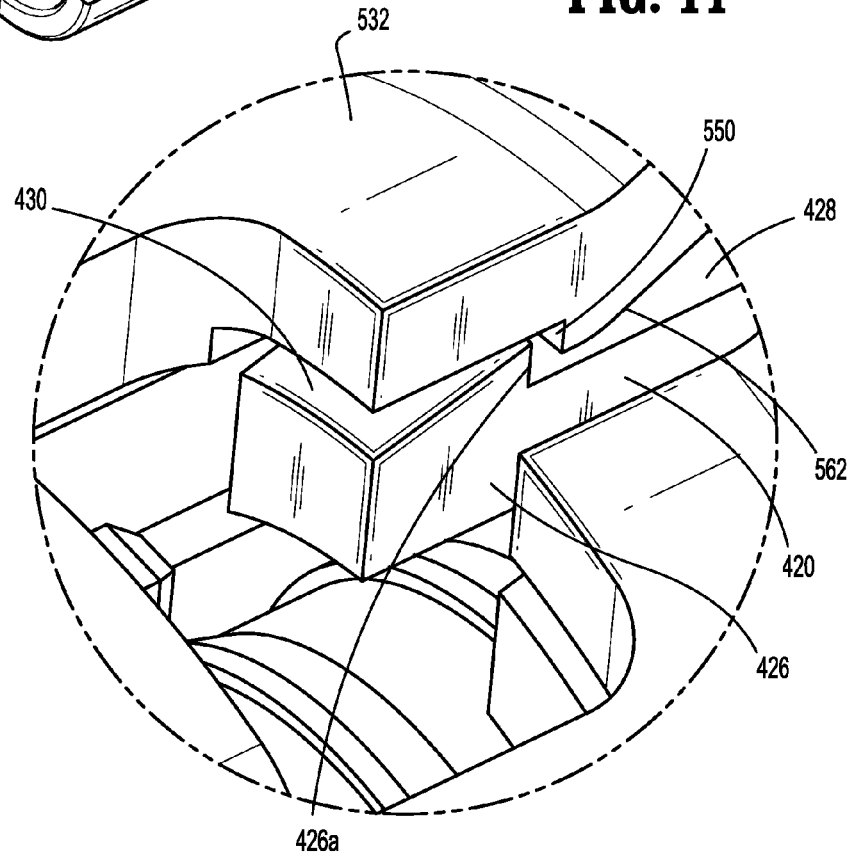
FIG. 12 is an enlarged view of the area of detail indicated in FIG. 11.

With reference to FIGS. 11-21, the engagement between pusher adapter 532 and knife carrier 420 is shown. With particular reference to FIGS. 12 and 13, proximal portion 422 of knife carrier 420 includes a plurality of latches 426, which are each configured to mechanically engage an engagement surface 550 (e.g., an undercut surface) of pusher adapter 532 upon a predetermined amount of longitudinal translation of knife carrier 420 with respect to pusher adapter 532. As can be appreciated, the engagement between latches 426 and engagement surfaces 550 prevent or substantially prevent portions of knife carrier 420 from translating distally beyond portions of pusher adapter 532.

More particularly, latches 426 of knife carrier 420 are disposed at a proximal end of flexible arms 428. Arms 428 are configured to deflect toward a radial center of knife carrier 420 to facilitate engagement/assembly between knife carrier 420 and pusher adapter 532. Further, to assemble knife carrier 420 and pusher adapter 532, knife carrier 420 is inserted in a proximal direction through a distal opening 560 of pusher adapter 532 until a ramped surface 430 of latches 426 contacts an angled surface 562 of an interior wall of pusher adapter 532. The contact between ramped surfaces 430 and angled surface 562, in combination with the proximal movement of knife carrier 420 with respect to pusher adapter 532, causes arms 428 to deflect radially inwardly, which allows a distal wall 426a of latches 426 to move proximally beyond engagement surfaces 550 of pusher adapter 532. Once in this position, arms 428 deflect radially outwardly (e.g., towards their biased position) such that distal walls 426a of latches 426 are physically prevented by engagement surfaces 550 of pusher adapter 532 from longitudinally translating distally therepast (see FIGS. 16 and 17). It is further envisioned that distal walls 426a of latches 426 include a ramped surface (e.g., the proximal portion of the ramped surface being closest to the radial center of knife carrier 420), and that engagement surfaces 550 of pusher adapter 532 include a complementary surface.

Figure 16:
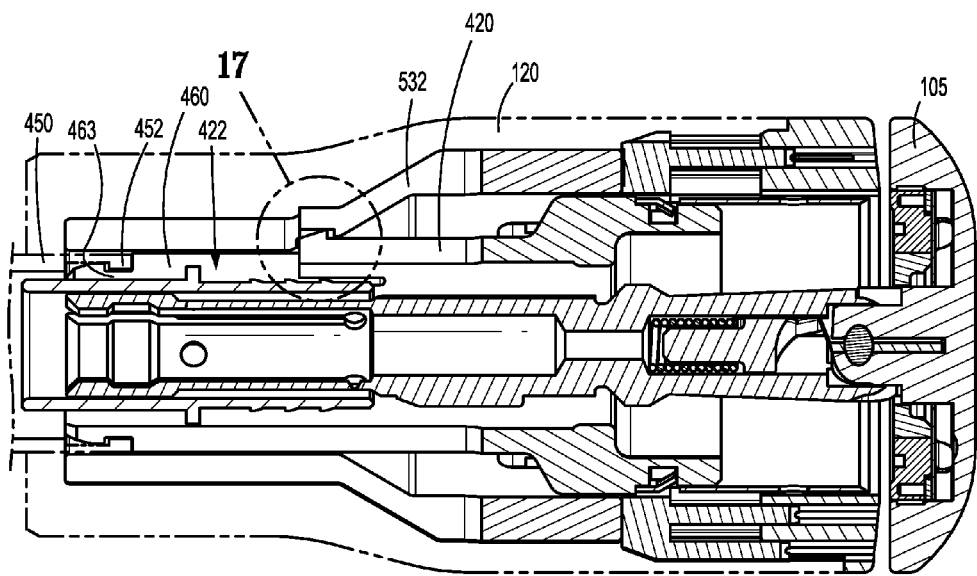
FIG. 16 is a cross-section view of the knife carrier engaged with the pusher adapter of FIG. 11.
Figure 17:
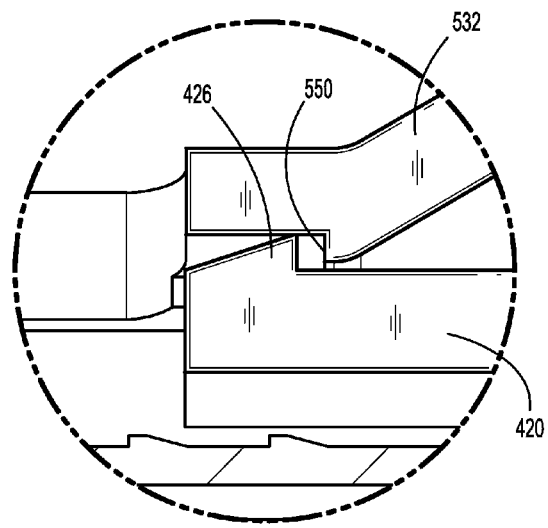
FIG. 17 is enlarged view of the area of detail indicated in FIG. 16.
Figure 18:
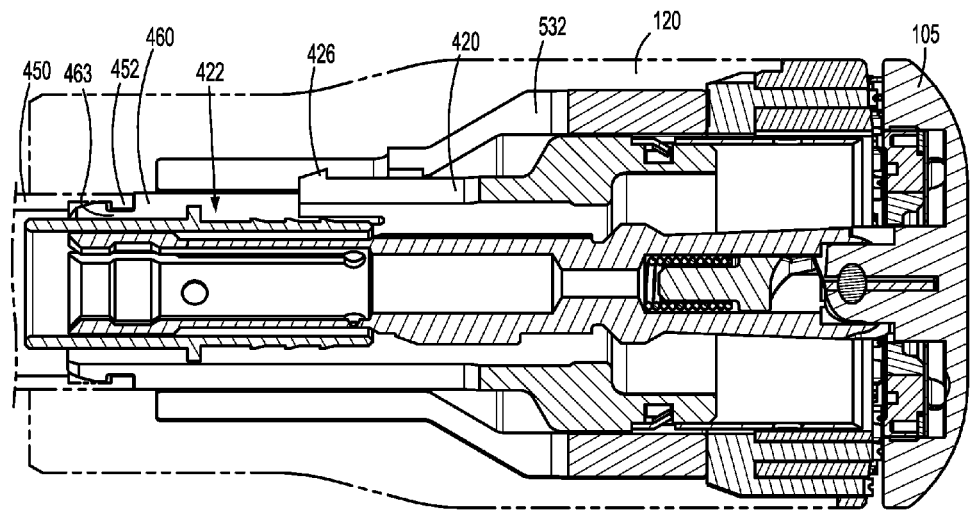
FIG. 18 is a cross-sectional view of the shell assembly illustrating the pusher adapter of FIG. 11 in an advanced position.
Figure 19:
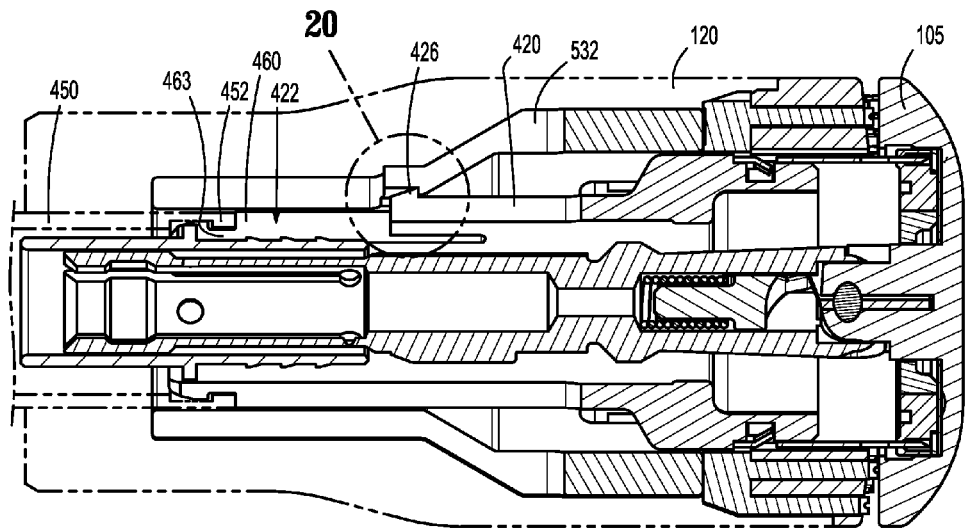
FIG. 19 is a cross-sectional view of the shell assembly illustrating the knife carrier of FIG. 11 in an advanced position.
Figure 20:
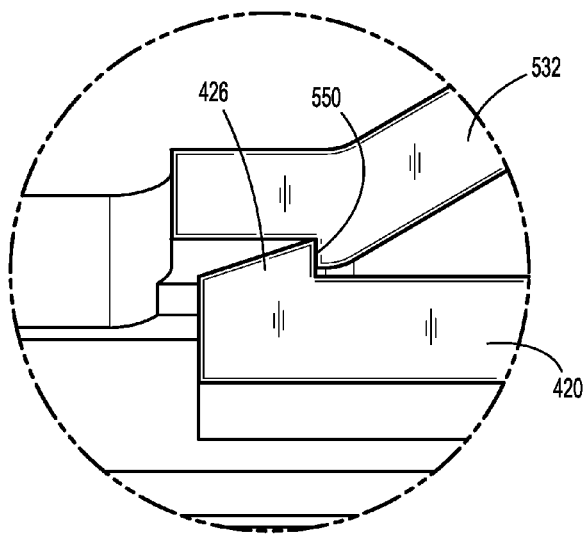
FIG. 20 is an enlarged view of the area of detail indicated in FIG. 19.
Figure 21:
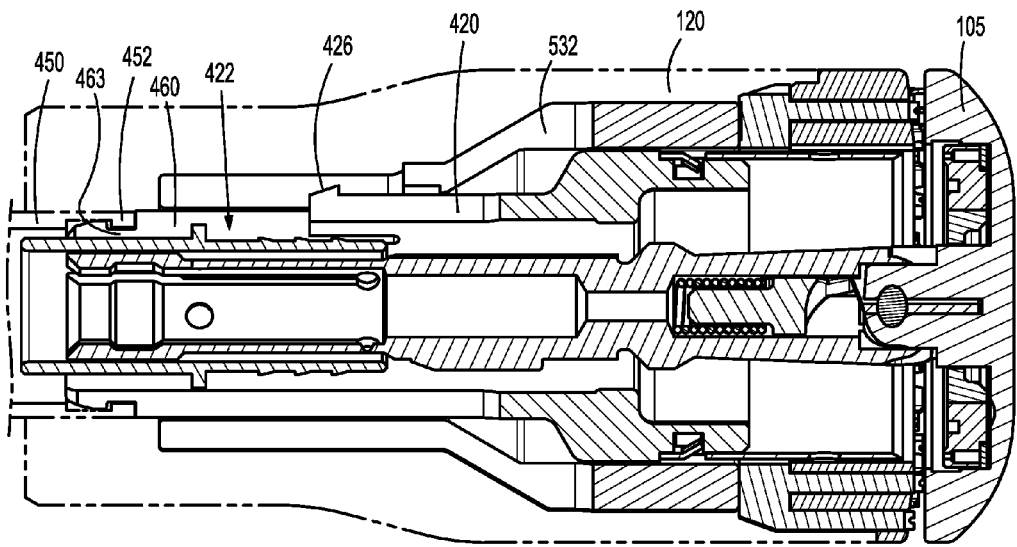
FIG. 21 is a cross-sectional view of the shell assembly illustrating the knife carrier of FIG. 11 in a retracted position.
Figure 22:
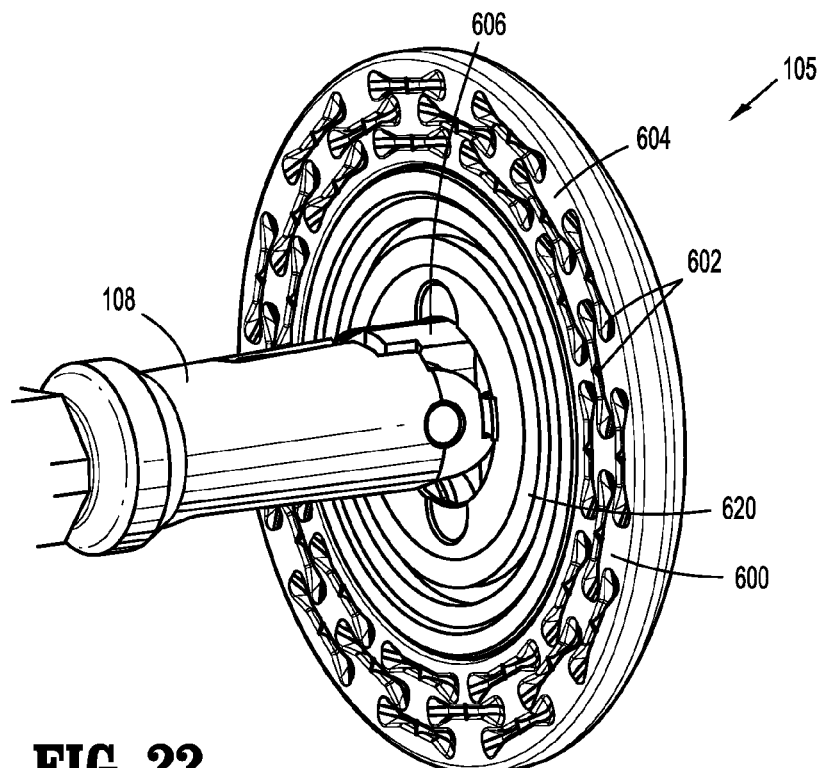
FIG. 22 is a perspective view of a portion of an anvil assembly including a cutting ring in accordance with embodiments of the present disclosure.
Figure 23:
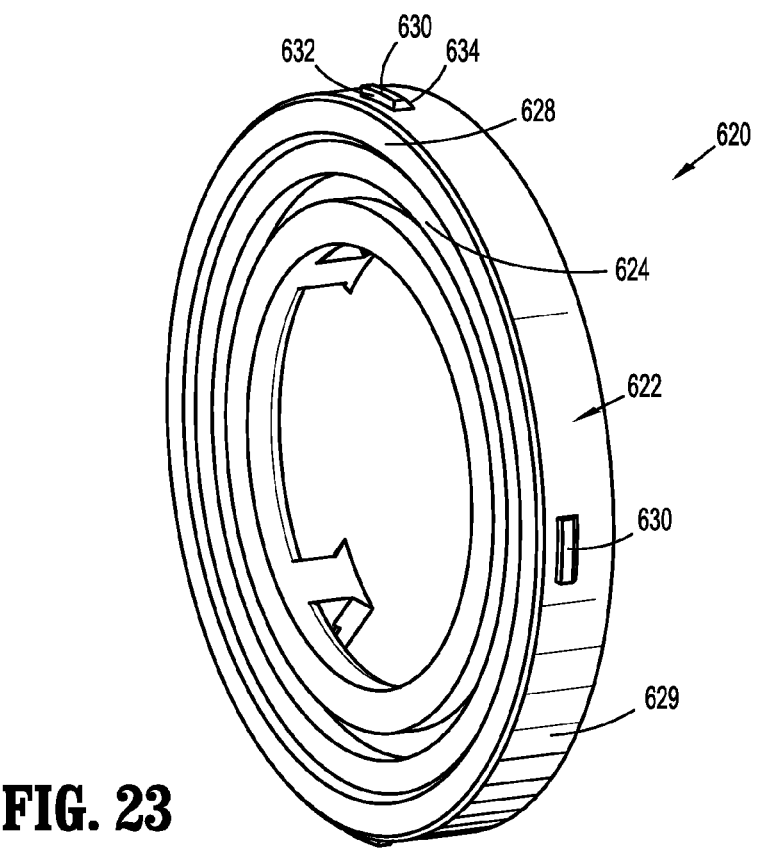
FIG. 23 is a perspective view of the cutting ring of FIG. 22.

Referring now to FIGS. 16-21, the relative movement between pusher adapter 532, knife carrier 420 and housing 120 is depicted. FIG. 16 illustrates pusher adapter 532 and knife carrier 420 in a retracted position. As shown in FIG. 17 (which is an enlarged view of a portion of FIG. 16), the orientation of latches 426 and engagement surfaces 550 limit the amount of distal travel of knife carrier 420 with respect to pusher adapter 532. As can be appreciated, this orientation prevents a user from cutting tissue prior to the tissue being stapled. FIG. 18 illustrates pusher adapter 532 in an advanced position, and knife carrier 420 in its retracted position (e.g., in response to a first actuation stroke to staple tissue). FIG. 19 illustrates pusher adapter 532 in its advanced position, and knife carrier 420 in an advanced position (e.g., in response to a second actuation stroke to cut tissue). As shown in FIG. 20 (which is an enlarged view of a portion of FIG. 19), the engagement between latches 426 and engagement surfaces 550 prevent additional distal travel of knife carrier 420 with respect to pusher adapter 532. FIG. 21 illustrates pusher adapter 532 in its advanced position, and knife carrier 420 in its retracted position (e.g., after tissue has been cut). As can be appreciated, the fact that pusher adapter 532 remains in its advanced position in this embodiment helps prevent inadvertent contact between knife 440 and a user of circular stapler 10, and between knife 440 and a patient.

In addition to the embodiment disclosed herein where a proximal portion 422 of knife carrier 420 is configured to engage snap ring 180, another embodiment is disclosed where proximal portion 422 of knife carrier 420 is configured to mechanically engage a drive member or sleeve 450 when knife carrier 420 mechanically engages pusher adapter 532. More particularly, in this embodiment, annular groove 463 of proximal portion 422 of knife carrier 420 is included on plurality of legs 460 (FIG. 13), with each leg 460 including a portion of annular groove 463 which is configured to engage a lip 452 of drive sleeve 450 (FIGS. 16, 18, 19 and 21). Further, legs 460 are configured to deflect radially inwardly, which allows proximal portion 422 of knife carrier 420 to be longitudinally translated proximally beyond lip 452 of drive sleeve 450, thus effectively coupling knife carrier 420 with drive sleeve 450 (see FIGS. 16, 18, 19 and 21, for example). As can be appreciated, in this embodiment, longitudinal translation of drive sleeve 450 (e.g., via a second actuation stroke of handle 24) causes a corresponding longitudinal translation of knife carrier 420.

Figure 24:
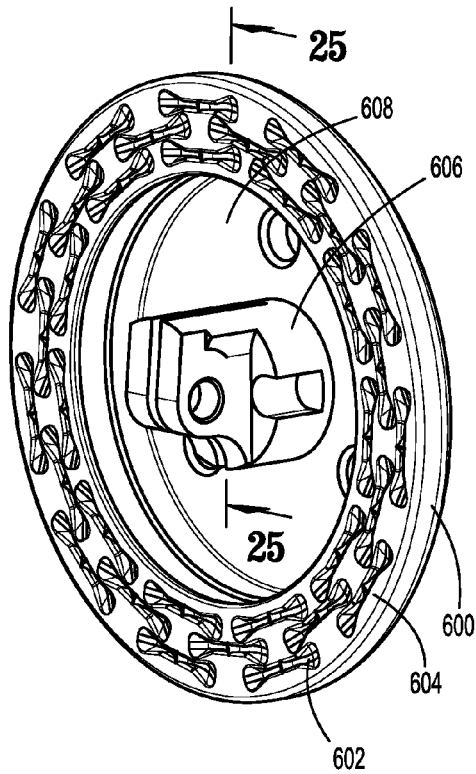
FIG. 24 is a perspective view of an anvil head of the anvil assembly of FIG. 22.
Figure 25:
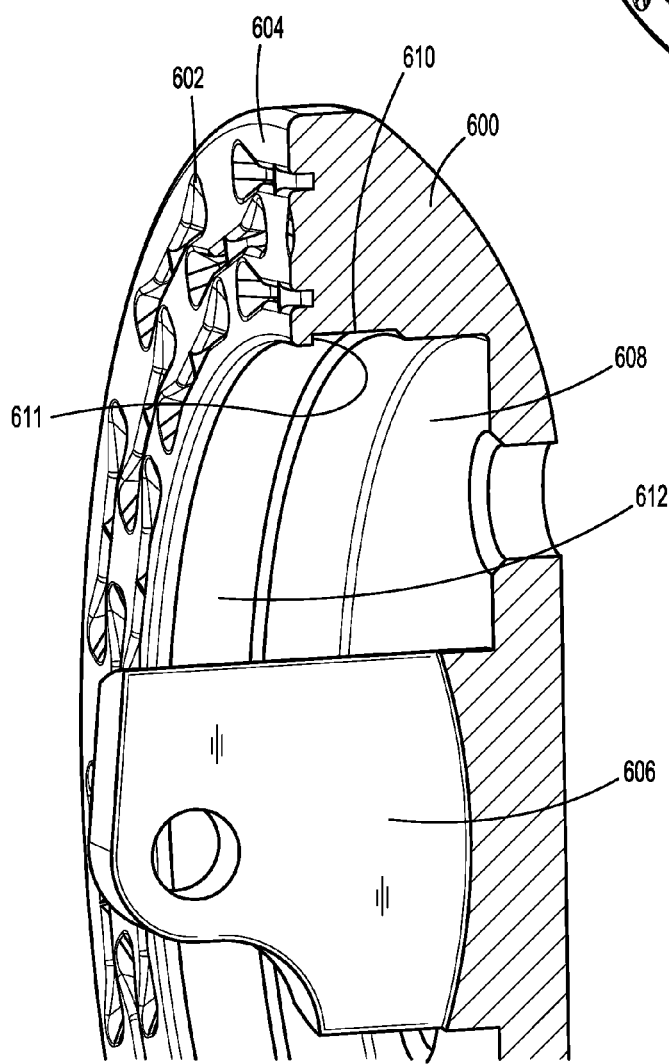
FIG. 25 is a cut-away perspective view of a portion of the anvil head of FIG. 24.

With reference to FIGS. 22-27, further details of anvil assembly 105 are illustrated in accordance with embodiments of the present disclosure. Anvil assembly 105 is longitudinally movable with respect to cartridge assembly 110, and includes a retention rod 108, which selectively connects anvil assembly 105 with the remainder of surgical stapler 10. Anvil assembly 105 includes an anvil head 600 and a cutting ring 620. Anvil head 600 includes a plurality of staple-deforming pockets 602 formed directly therein (i.e., without the inclusion of a traditional anvil plate). Pockets 602 are configured to receive legs of the staples ejected from staple cartridge 110 and to deform the legs into an appropriate shape. In the illustrated embodiment, pockets 602 are disposed in three rows and annularly extend along a tissue-contacting surface 604 of anvil head 600. Anvil assembly 105 also includes an attachment member 606 extending proximally from anvil head 600. Attachment member 606 is configured to pivotably engage retention rod 108. An annular cavity 608 is defined by anvil head 606 and is disposed around (e.g., surrounding) attachment member 606 (FIGS. 24 and 25). It is envisioned that the entirety of anvil head 606 is monolithically formed and/or is made of the same material.

Cutting ring 620 is configured for positioning within annular cavity 608 of anvil head 600. More particularly, cutting ring 620 includes an outer ring 622, an inner ring 624, an annular knife channel 626 disposed between outer ring 622 and inner ring 624, and a severable portion 628 disposed proximally-adjacent knife channel 626. Severable portion 628 is configured to be cut by knife 440 (see FIGS. 26 and 27) during the cutting stroke of circular instrument 10.

Cutting ring 620 also includes a plurality of tabs 630 disposed around its outer annular edge 622. Tabs 630 are configured to mechanically engage a groove 610 disposed around an inner annular surface 612 of anvil head 600. Any number of tabs 630 (including a single tab 630 that extends along the entire surface 612) may be included on cutting ring 620. More particularly, each tab 630 includes a proximal surface 632 that is substantially perpendicular to annular edge 629, and a distal surface 634 that is angled with respect to annular edge 629 and with respect to proximal surface 632.

Distal surface 634 of tab 630 is configured to facilitate assembly between cutting ring 620 and anvil head 600. That is, during assembly, cutting ring 620 is inserted into annular cavity 608 in a proximal-to-distal direction such that distal surface 634 contacts a portion of anvil head 600 and causes cutting ring 620 to deflect radially inwardly to allow tabs 630 to extend distally beyond a lip 611 formed by a proximal surface of groove 610. It is further envisioned that cutting ring 620 is made of a flexible material (e.g., polyethylene) to further facilitate assembly.

Figure 26:
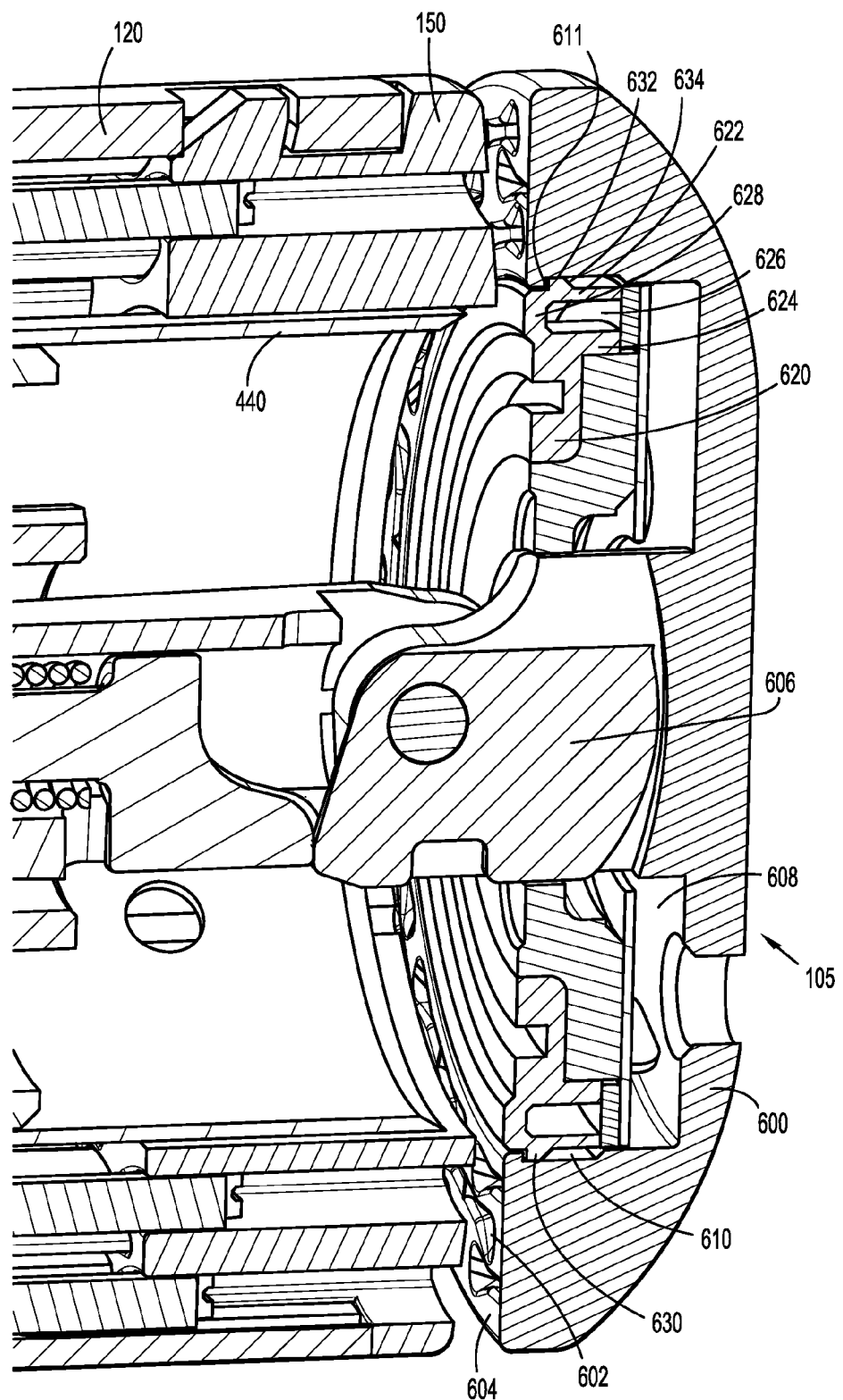
FIG. 26 is a cut-away perspective view of a portion of the anvil assembly of FIG. 22 engaged with the shell assembly of the present disclosure, and illustrating a knife in a proximal position.
Figure 27:
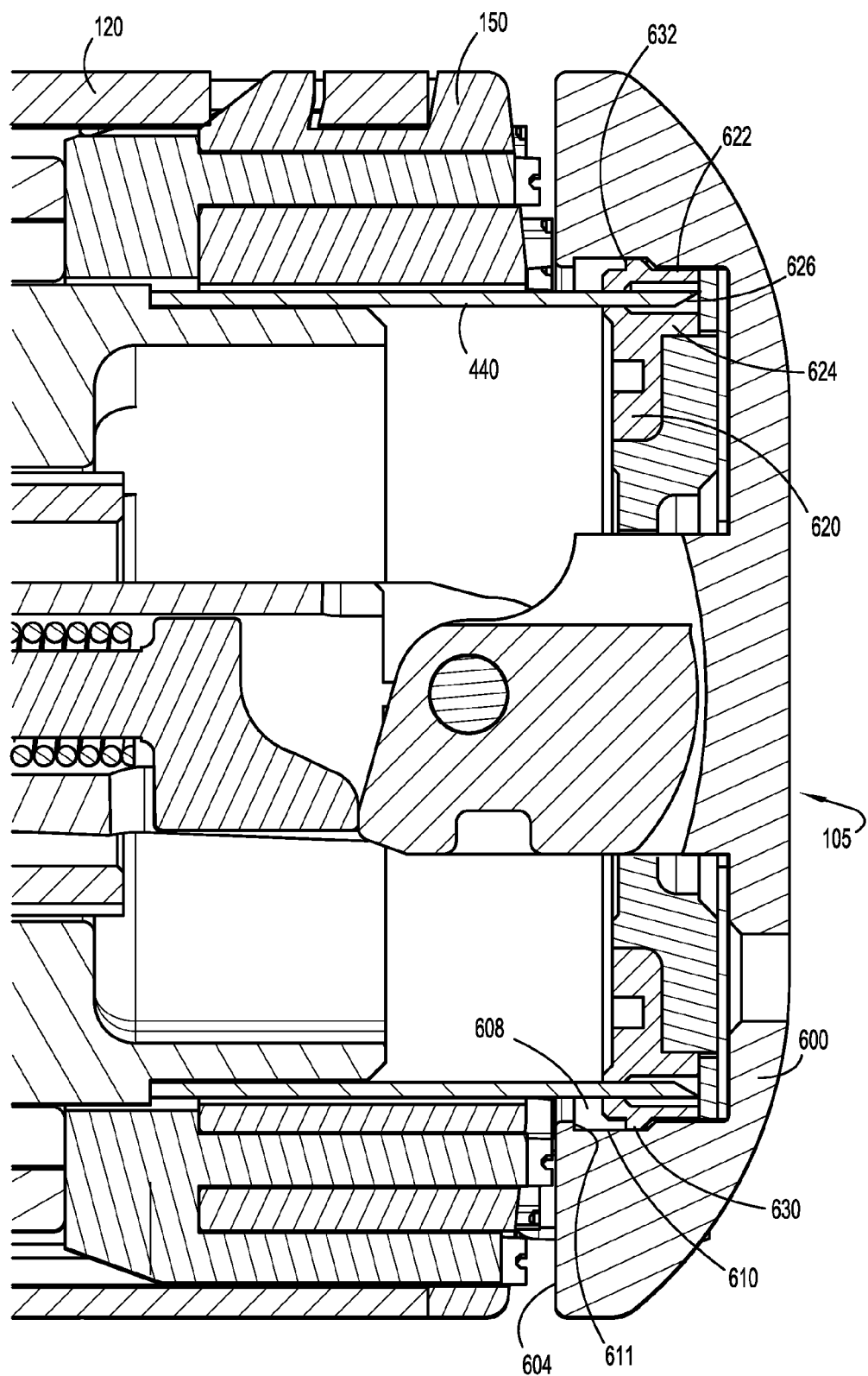
FIG. 27 is a cut-away perspective view of the portions of the anvil assembly and shell assembly of FIG. 26, and illustrating the knife in an advanced position.

With reference to FIGS. 26 and 27, proximal surface 632 of tabs 630 is configured to engage lip 611 of groove 610 to help ensure engagement therebetween. More particularly, in use, when knife 440 is advanced to cut tissue, knife 440 also penetrates severable portion 628, which separates outer ring 622 and inner ring 624 (see FIG. 27). As shown in FIG. 27 when compared to FIG. 26, distal advancement of knife 440 also pushes cutting ring 620 distally within cavity 608. The engagement between outer ring 622 of cutting ring 620 and anvil head 600 helps ensure outer ring 622 is removed from the surgical site when anvil head 600 is removed.

Figure 28:
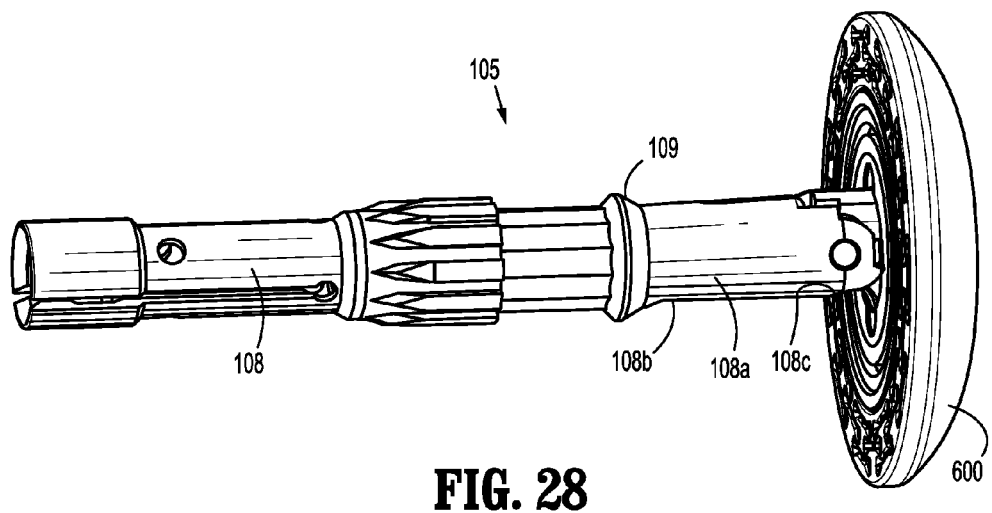
FIG. 28 is a perspective view of an anvil assembly in accordance with an embodiment of the present disclosure.
Figure 29:
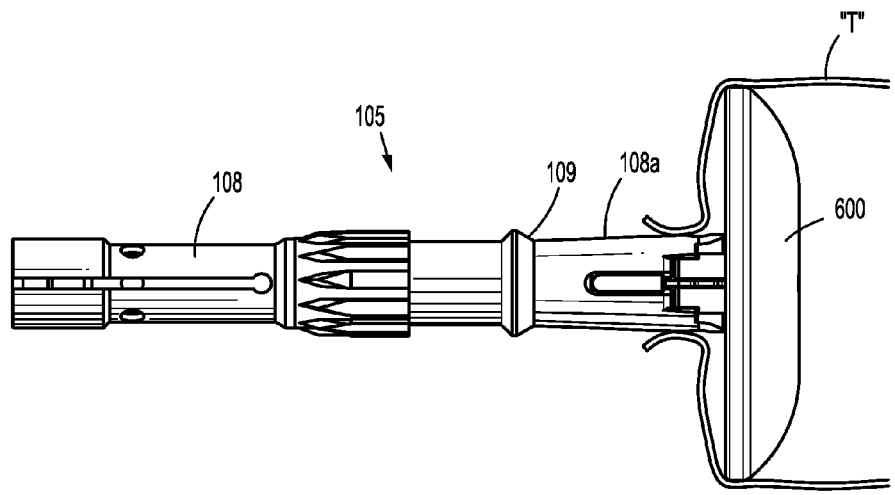
FIG. 29 is a side view of the anvil assembly of FIG. 28 shown with the anvil head within tissue.
Figure 30:
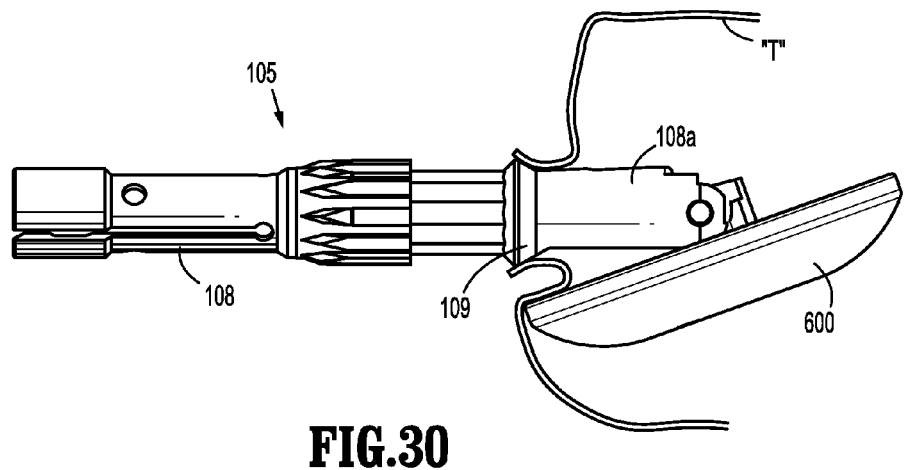
FIG. 30 is a side view of the anvil assembly of FIGS. 28 and 29 shown with the anvil head in a titled position and within tissue.
Figure 31:
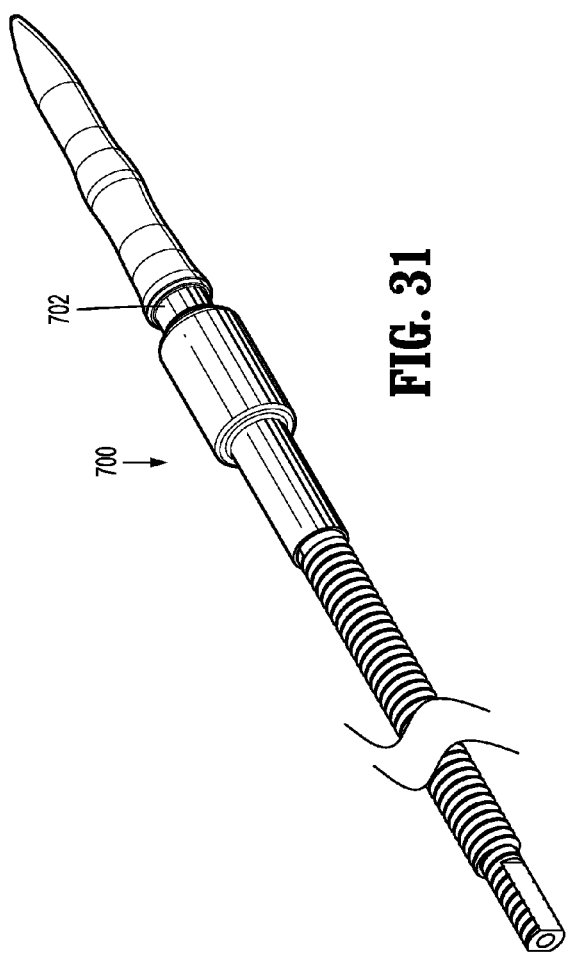
FIG. 31 is a perspective view of a first trocar in accordance with the present disclosure.

With reference to FIGS. 28-30, further details of anvil assembly 105 and its retention rod 108 are illustrated in accordance with embodiments of the present disclosure. As discussed above, anvil head 600 is pivotably engaged with retention rod 108, e.g., to facilitate removal of anvil assembly 105 from within tissue. In use, tissue "T" is tied or purse-string sutured to a distal portion 108a of retention rod 108. Distal portion 108a is defined as being disposed distally of a lip 109, which is configured to limit proximal travel of tissue "T," and as being the portion of retention rod 108 that is configured to contact tissue "T."

In the illustrated embodiment, distal portion 108a of retention rod 108 is tapered along its entire length. Further, distal portion 108a includes a continuous taper, which includes a concave portion 108b and a convex portion 108c. As shown, distal portion 108a lacks a stepped configuration and lacks abrupt angle changes. It is envisioned that this tapered configuration of distal portion 108a of retention rod 108 helps purse-string sutured tissue "T" easily slide proximally when anvil head 600 tilts and thus urges tissue "T" proximally (see FIG. 30).

With reference to FIGS. 31-34, retention rod 108 of anvil assembly 105 is configured to selectively engage a trocar 700 extending distally beyond cartridge assembly 110. More particularly, this embodiment illustrates a first retention rod 108' that is configured to engage a first trocar 700' (FIG. 32), and a second retention rod 108" that is configured to engage a second trocar 700" (FIG. 32A). Here, however, first retention rod 108' cannot properly engage second trocar 700" (FIG. 33), and second retention rod 108" cannot properly engage first trocar 700' (FIG. 34). That is, engagement between first retention rod 108' and first trocar 700', and between second retention rod 108" and second trocar 700" would result in the two components securely engaging each other such that longitudinal translation of the first component (e.g., first retention rod 108') in the opposite direction of the second component (e.g., first trocar 700') would result in a corresponding amount of longitudinal translation of the second component. Conversely, an attempted engagement between first retention rod 108' and second trocar 700", or between second retention rod 108" and first trocar 700' would result in the two components being free from secure engagement with each other such that longitudinal translation of the first component (e.g., first retention rod 108') in the opposite direction of the second component (e.g., second trocar 700") would cause the first component to move away from the second component.

It is envisioned that each of first retention rod 108' and first trocar 700' are configured for use with a particular configuration of staples. For instance, it is envisioned that first retention rod 108' is part of an anvil assembly 105 that includes two rows of staple-deforming pockets 602, and that first trocar 700' is part of/usable with a shell assembly 100 including two rows of pusher elements 546 and a staple cartridge 150 having two rows of staples "S." Likewise, it is envisioned that second retention rod 108" is part of an anvil assembly 105 that includes three rows of staple-deforming pockets 602, and that second trocar 700" is part of/usable with a shell assembly 100 including three rows of pusher elements 546 and a staple cartridge 150 having three rows of staples "S."

Figure 32:
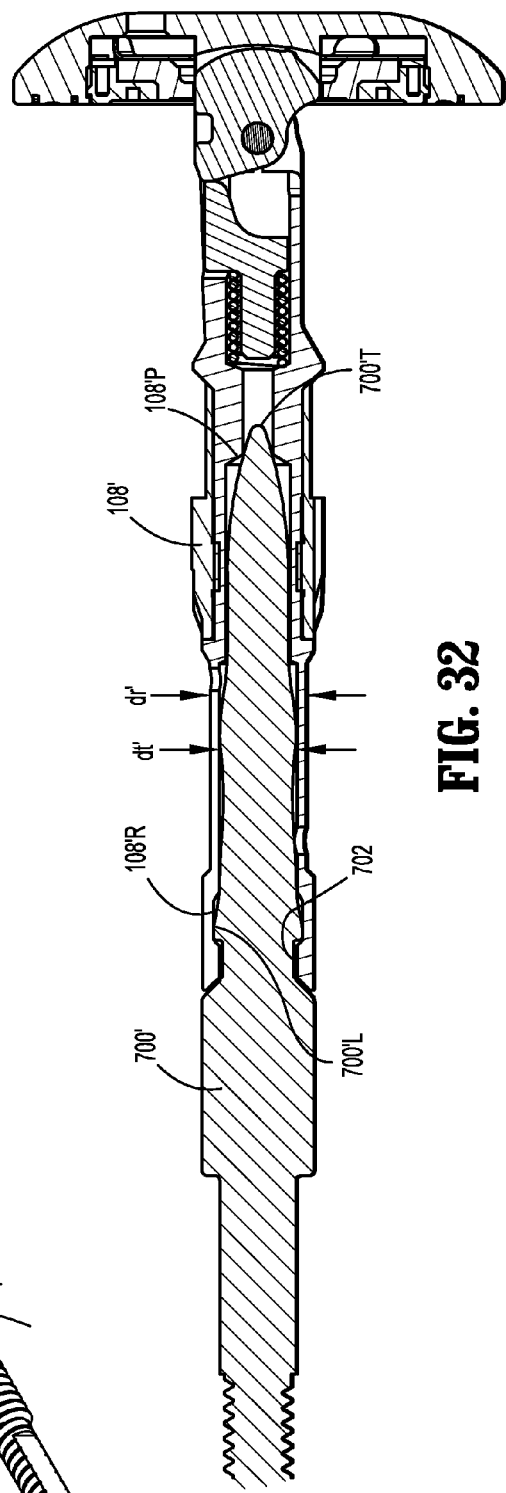
FIG. 32 is a longitudinal cross-sectional view of the first trocar of FIG. 31 engaged with a first retention rod.
Figure 32A:
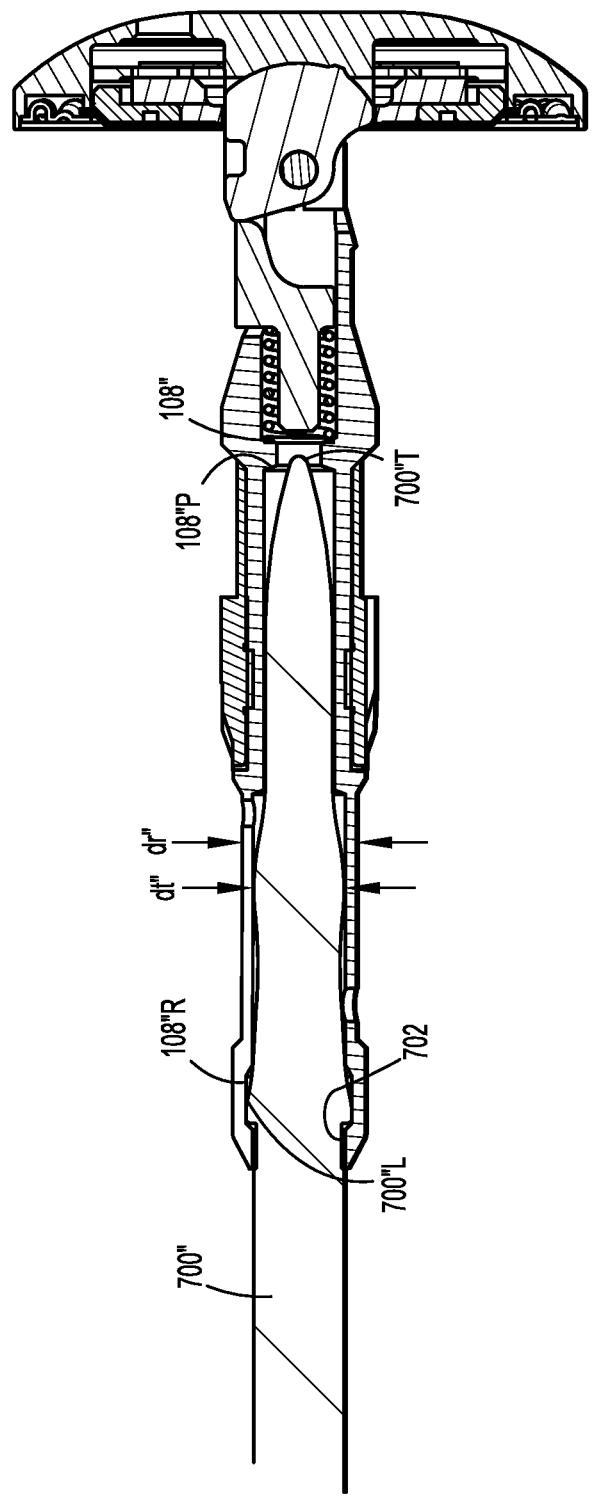
FIG. 32A is a longitudinal cross-sectional view of a second trocar engaged with a second retention rod in accordance with the present disclosure.
Figure 35:
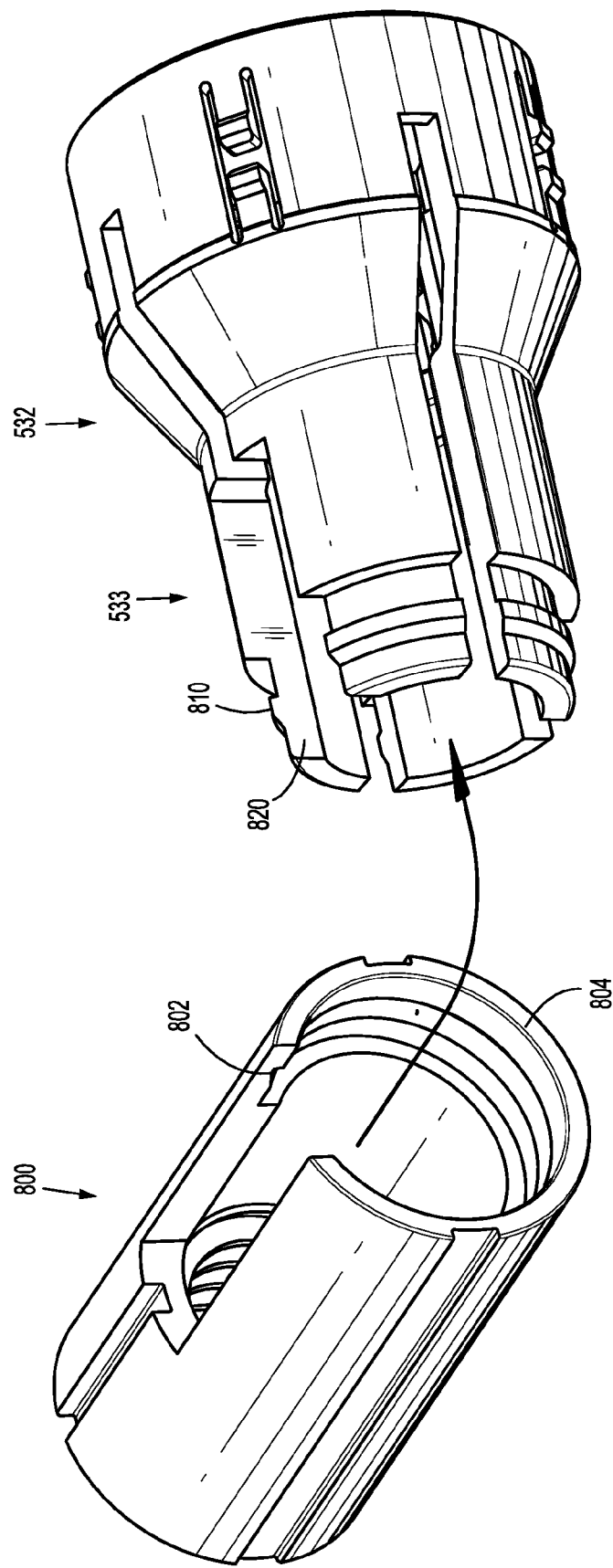
FIG. 35 is a perspective, assembly view of a portion of a drive member and a pusher adapter in accordance with embodiments of the present disclosure.

More particularly, first retention rod 108' includes a recess 108'R that is configured to engage a lip 700'L extending from first trocar 700' (FIG. 32). Similarly, second retention rod 108" includes a recess 108"R that is configured to engage a lip 700"L extending from second trocar 700" (FIG. 32A). The geometry of retention rods 108', 108" and trocars 700', 700" enable this mistake-proof engagement therebetween. More particularly, and with reference to FIGS. 32 and 32A, it is envisioned and illustrated that first retention rod 108' includes a larger diameter dr' than a corresponding diameter dr" of second retention rod 108". Here, first trocar 700' includes a larger diameter dt' than a corresponding diameter dt" of second trocar 700". Additionally, it is envisioned and illustrated that the distance between recess 108'R and a proximal lip 108'P of first retention rod 108' is shorter than the distance between recess 108"R and a proximal lip 108"P of second retention rod 108". Likewise, the illustrated embodiments show that the distance between lip 700'L and a tip 700'T of first trocar 700' is shorter than a corresponding distance between lip 700"L and a tip 700"T of second trocar 700".

With reference to FIGS. 33 and 34, recess 108'R of first retention rod 108' is not able to properly engage lip 700"L of second trocar 700" (FIG. 33), and recess 108"R of second retention rod 108" is not able to properly engage lip 700'L of first trocar 700' (FIG. 34), e.g., due to the various geometries discussed above. As discussed above, proper engagement between a retention rod 108 and a trocar 700 is the secure engagement therebetween.

Additionally, it is envisioned that each of first trocar 700' and second trocar 700" includes an indicator 702 that is perceptible to a user if there is not proper engagement between a retention rod 108 and a trocar 700 (e.g., if a user attempts to engage first retention rod 108' with second trocar 700", or vice versa). The present disclosure includes indicators 702 that provide visual (e.g., a colored band, letters, symbols, etc.), audio (e.g., beeps, clicks, etc.) and/or tactile (e.g., vibration, etc.) information. As illustrated, indicator 702 is not perceptible (e.g., visible) when there is proper engagement between a retention rod 108 and a trocar 700. Alternatively, it is envisioned that indicator 702 is perceptible to a user if there is proper engagement between a retention rod 108 and a trocar 700, and indicator 702 is non perceptible to a user if there is not proper engagement between a retention rod 108 and a trocar 700.

Referring now to FIGS. 35-39, details regarding the engagement between drive member 800 and pusher adapter 532 are shown in accordance with an embodiment of the present disclosure. During use of this embodiment of circular stapler 10, an initial actuation stroke is performed to fire staples "S" into tissue. Here, drive member 800 (or a portion thereof) is distally advanced into engagement with pusher adapter 532, and continued advancement of drive member 800 causes pusher adapter 532 to urge pusher member 540 distally to eject the staples "S" (as discussed above). Next, drive member 800 and pusher adapter 532 are retracted proximally (while pusher member 540 remains in its advanced position). Then, in response to a second actuation stroke, for example, drive member 800 and pusher adapter 532 are again advanced distally so that pusher adapter 532 urges and/or engages knife carrier 420 distally to sever tissue. As can be appreciated, this embodiment differs from embodiments described above, as here, independent actuation strokes are completed by the same drive member 800 completing two strokes (as opposed to the use of two separate drive members being used).

Figure 36:
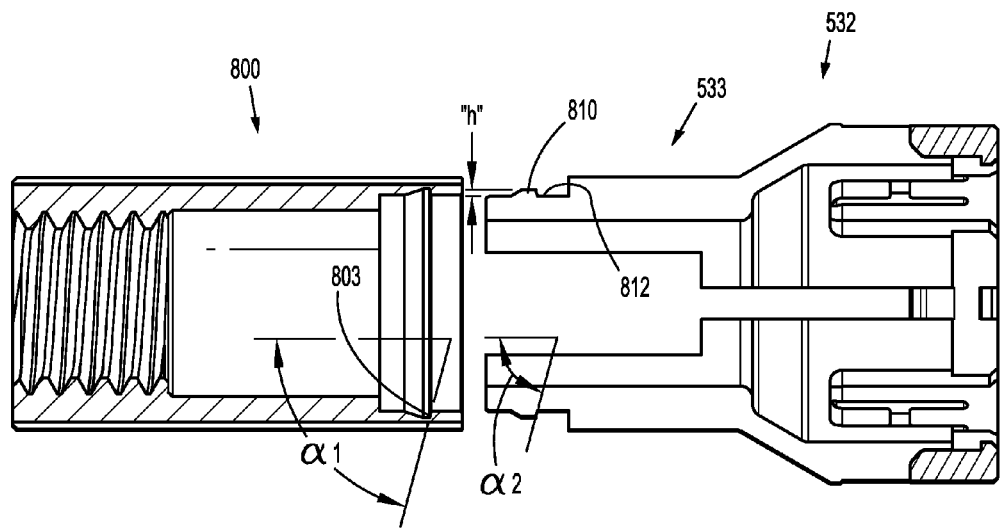
FIGS. 36-38 are longitudinal cross-sectional views of the portion of the drive member and the pusher adapter of FIG. 35 illustrated in various stages of engagement.
Figure 37:
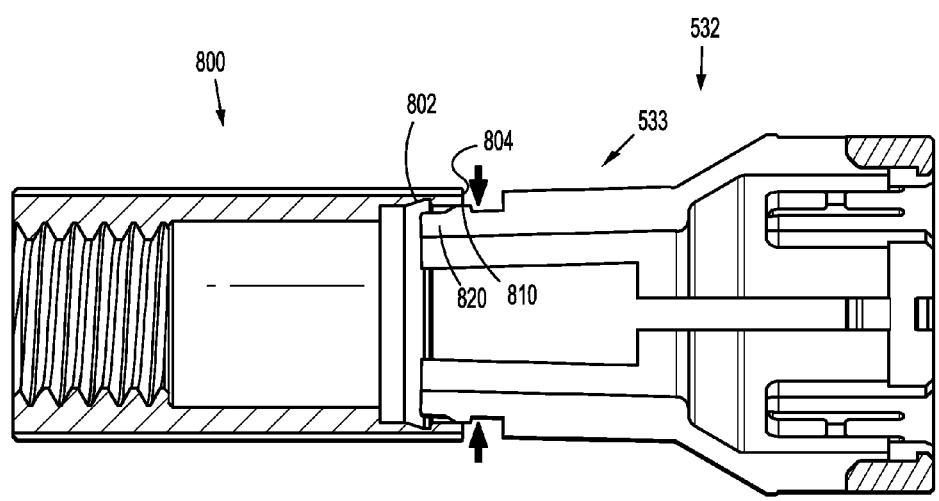
Figure 38:
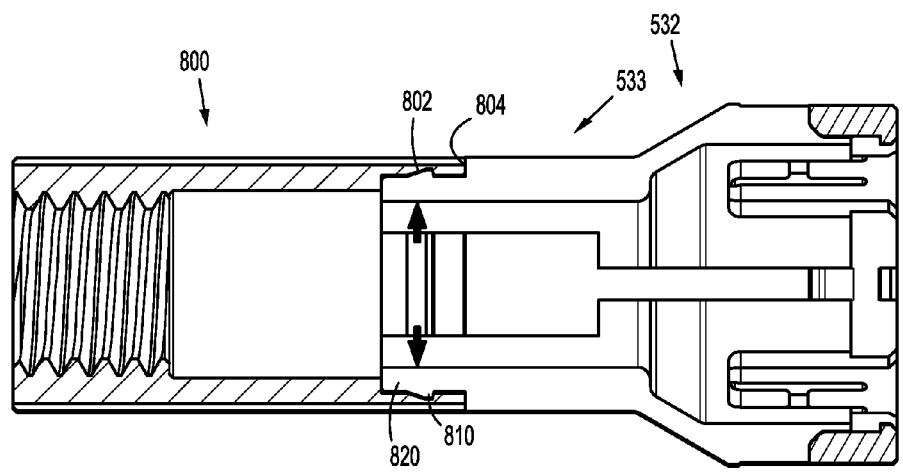
Figure 39:
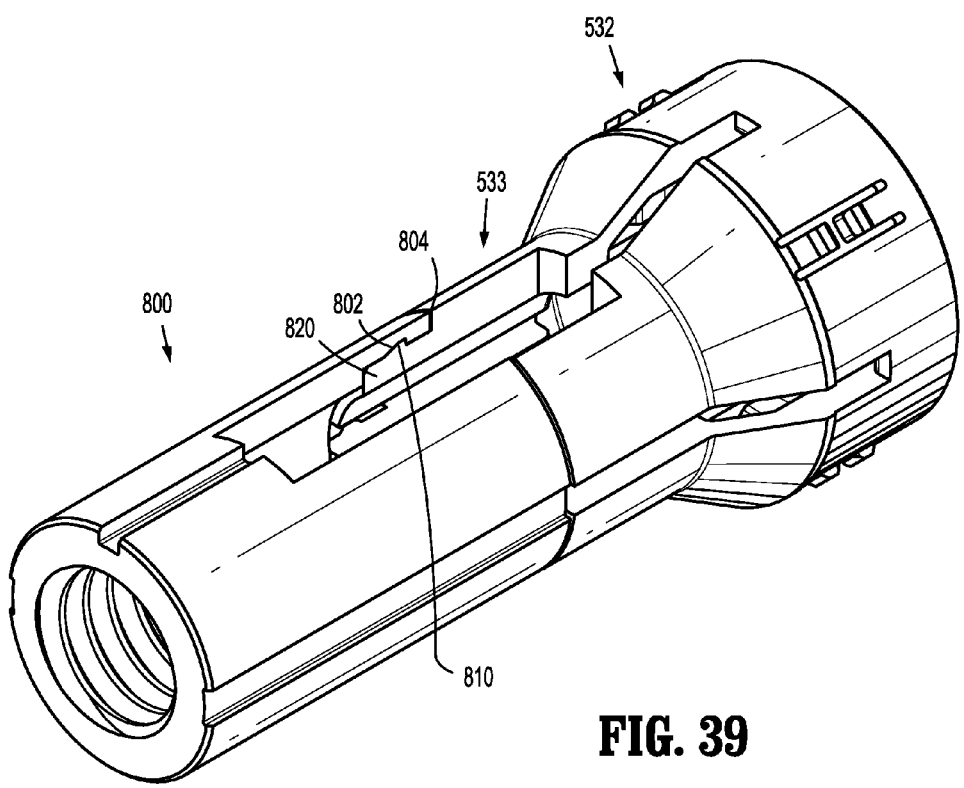
FIG. 39 is a perspective view of the portion of the drive member and the pusher adapter of FIG. 35 in an engaged position.

FIGS. 35-39 illustrate various features of the engagement between drive member 800 and pusher adapter 532, which are configured to help facilitate engagement therebetween, and to help ensure engagement therebetween during advancement and refraction of drive member 800. More particularly, drive member 800 (e.g., an adapter nut) includes a recess 802 (e.g., an annular recess) configured to engage tabs 810 on fingers 820 on proximal portion 533 of pusher adapter 532. As drive member 800 is distally translated and contacts pusher adapter 532, a distal surface 804 of drive member 800 contacts tabs 810 and forces tabs 810 and fingers 820 radially inward (FIG. 37). Continued advancement of drive member 800 with respect to pusher adapter 532 causes tabs 810 and fingers 820 to move radially outward, such that tabs 810 are within recess 802 (FIGS. 38 and 39).

In disclosed embodiments and with particular reference to FIGS. 36 and 37, a distal wall 803 of recess 802 forms an angle $\alpha 1$ of between about 70° and about 90° with respect to the longitudinal axis A-A. In embodiments, angle $\alpha 1$ is between about 70° and about 80°, or between about 75° and about 78°. Similarly, a distal wall 812 of tabs 810 forms an angle $\alpha 2$ of between about 70° and about 90° with respect to the longitudinal axis A-A. In embodiments, angle $\alpha 2$ is between about 70° and about 80°, or between about 75° and about 78°. It is envisioned that the angles formed by distal wall 803 of recess 802 and by distal wall 812 of tables 810 are equal, substantially equal, or differently from each other.

Additionally, in disclosed embodiments, the height "h" of tabs 810 (and the corresponding depth of the corresponding portion of recess 802) is between about 0.010 inches and about 0.020 inches (see FIG. 36). In embodiments, height "h" is approximately equal to 0.015 inches.

It is further disclosed that pusher adapter 532 (or at least fingers 820 thereof) is made from glass-filled polycarbonate. Here, it is envisioned that the percentage of glass is between about 20% and about 40% (e.g., about equal to 30%).

It is envisioned that the combination of the angles of distal walls 803 and 812, the height "h" of tabs 810, and the material that pusher adapter 532 is made from all contribute to a secure engagement between pusher adapter 532 and drive member 800, and result in an optimum amount of force necessary to disengage pusher adapter 532 from drive member 800.

Figure 40:
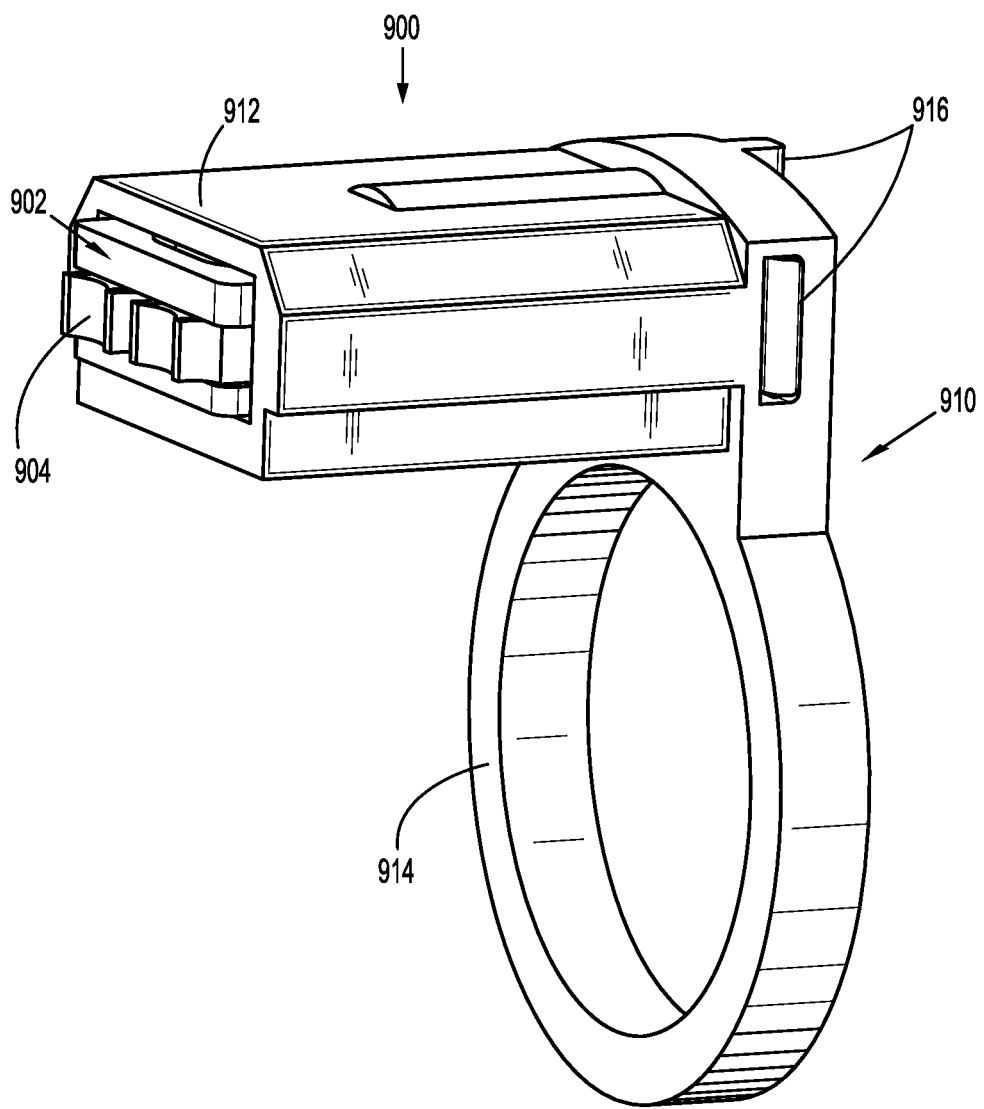
FIG. 40 is a perspective view of communication chip assembly in accordance with embodiments of the present disclosure.
Figure 41:
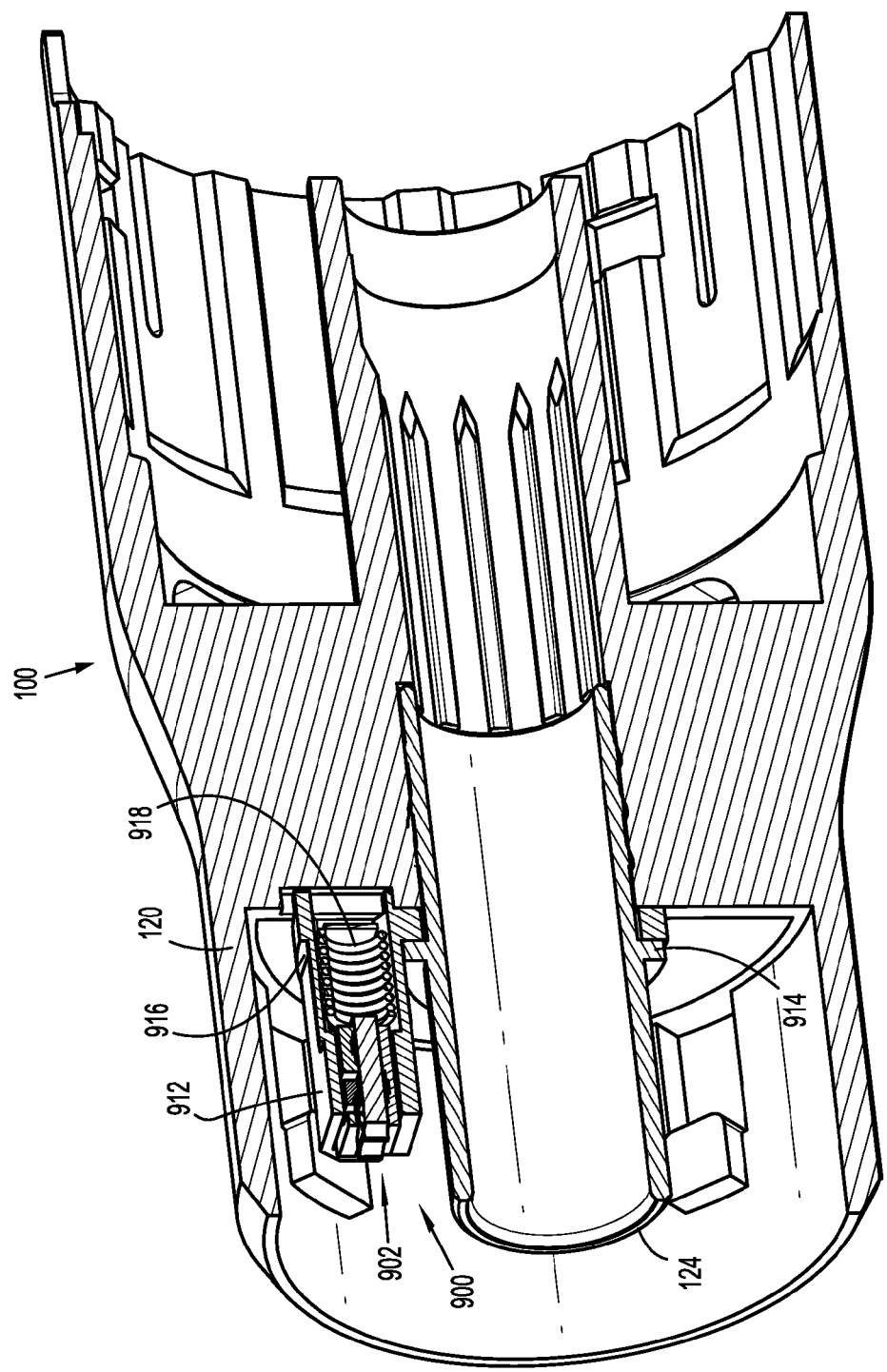
FIG. 41 is a perspective, cut-away view of the communication chip assembly of FIG. 40 positioned within a shell assembly.

With reference to FIGS. 40 and 41, the present disclosure also includes a communication chip assembly 900, which is configured to communicate various information to and from other portions of circular stapler 10. With particular reference to FIG. 40, communication chip assembly 900 includes a case 910 housing a communication chip 902. Case 910 includes a tube portion 912 and a ring portion 914. With reference to FIG. 41, tube portion 912 of case 910 is configured to be press-fit into housing 120 of shell assembly 100. Ring portion 914 is configured for surrounding (or at least partially surrounding) inner cylindrical body 124 of housing 120 (e.g., via a compression-fit arrangement). Additionally, case 910 includes a plurality of tabs 916 that are configured to engage respective slots/detents (not explicitly shown) in housing 120 to help prevent rotation of communication chip assembly 900 with respect to housing 120.

A proximal portion of communication chip 902 includes a plurality of contacts 904 for engaging contact pins of a portion (e.g., adaptor—not shown) of circular stapler 10. As can be appreciated, this engagement between contacts 904 and contact pins allows information to be communicated from one portion of circular stapler 10 (e.g. handle assembly 20) to shell assembly 100. Further, communication chip 902 is spring-loaded via a biasing member 918 in a proximal direction (e.g., to allow for positional length tolerance of the contact pins in the adapter).

It is envisioned that communication chip 902 includes both read and write capability, and is particularly useful with a powered surgical stapler. The read capability of communication chip 902 enables communication of various features of shell assembly 100 to handle assembly 20. For example, communication chip 902 can store and relay information relating to cartridge size, staple length, and clamp-up distance. Once this information is received by handle assembly 20, for example, firing forces and firing stroke can be adjusted accordingly. The write capability of communication chip 902 enables handle assembly 20, for example, to encode a used (i.e., fired) cartridge assembly 110 to prevent reuse or attempted firing of a staple-less cartridge assembly 110. Further details of communication components (e.g., chips, transmitters, control modules, etc.) are disclosed in U.S. patent application Ser. No. 13/545,362, which was filed on Jul. 10, 2012, the entire contents of which being incorporated by reference herein. Further communication components are disclosed in U.S. application Ser. Nos. 13/968,634 and 13/968,563, both filed on Aug. 16, 2013, the entire disclosures of which are hereby incorporated by reference herein.

The use of circular stapler 10 will now be described as it pertains to various embodiments of the present disclosure. In use, circular stapler 10 is operated in a manner substantially similar to a traditional circular stapler. Once oriented such that the tissue to be stapled is received between cartridge assembly 110 and anvil assembly 105, and anvil assembly 105 is approximated towards cartridge assembly 110 via rotation of approximation knob 26, trigger 24 may be squeezed to cause the actuation of handle assembly 20. Actuation of handle assembly 20 causes a first advancement of a drive assembly (e.g., 800) which engages and causes the advancement of pusher assembly 530. During the first or staple forming stroke, pusher assembly 530 is moved relative to housing 120 and knife assembly 400, while knife assembly 400 remains stationary relative to housing 120. In this manner, during the first or staple forming stroke of circular stapler 10 only the staple forming function is performed. Accordingly, the force required for completion of the first stroke of circular stapler 10 does not include the force necessary to also cut the tissue simultaneously therewith.

Upon completion of the first or staple forming stroke, trigger 24 is released to permit the retraction of the drive member and pusher adapter 532 of pusher assembly 530. In various embodiments, pusher adapter 532 is retracted to a position proximal of its initial position. For example, it is envisioned that pusher adapter 532 is retracted about 0.25 inches farther proximally from its initial starting position. In this retracted position, notch 535 formed in the distal end of pusher adapter 532 is aligned with snap ring 180 thereby allowing snap ring 180 to expand from the first or compressed condition to the second or uncompressed condition.

A subsequent squeezing or actuation of trigger 24 causes a second advancement of the drive member and pusher adapter 532. Advancement of pusher adapter 532 causes engagement of ledge 536 of pusher adapter 532 with snap ring 180. Since snap ring 180 remains engaged with knife carrier 420 in this position, advancement of pusher adapter 532 also causes the advancement of knife assembly 420. Advancement of circular knife 440 of knife assembly 400 causes the cutting of tissue positioned between cartridge assembly 110 and anvil assembly 105. Because staples "S" were ejected and formed during the first stroke of circular stapler 10, and pusher member 540 remained in the advanced position upon retraction of pusher adapter 532 following the first or staple forming stroke, the force required to complete the second or cutting stroke of circular stapler 10 is less then the force that would be necessary to complete both the staple ejecting/forming and tissue cutting procedure. It is envisioned that the force provided by the drive member during the second stroke would be sufficient to disengage any securing mechanism maintaining knife assembly 400 relative to inner cylindrical housing 124 of housing 120. Such securing mechanism may include protrusions (not shown) formed on the inner surface of knife carrier 420 and/or on the outer surface of inner cylindrical portion 124 of housing 120 configured to be received within detents (not shown) formed on the other of the outer surface of inner cylindrical portion 124 and/or on the inner surface of knife carrier 420 such that knife assembly 400 is permitted to advance distally relative to housing 120.

Upon completion of the tissue cutting stroke, pusher adapter 532 is retracted proximally to one of the initial position or the retracted position. As discussed above, pusher assembly 530 and knife assembly 400 may be configured such that either or both of pusher assembly 530 and knife assembly 400 are retracted following the second or cutting stroke of circular stapler 10. Retraction of pusher adapter 532 to one of the initial or retracted positions causes disengagement of pusher member 540 from pusher adapter 532. In this manner, pusher member 540 and empty staple cartridge 150 may be separated or unloaded from housing 120 and replaced with a new pusher member 540 and/or staple cartridge 150.

Further details regarding the operation of circular stapler 10, including the operation of cartridge assembly 110, will now be described as it pertains to various embodiments of the present disclosure. In the initial condition, pusher assembly 530 is received between outer and inner cylindrical portions 122, 124 of housing 120. Knife assembly 400 is received within longitudinal passage 531 of pusher adapter 532 and about inner cylindrical portion 124 of housing 120. Staple cartridge 150 is in operative engagement with a distal portion of housing 120 to operably retain pusher assembly 530 and knife assembly 400 within housing 120. Snap ring 180 is in the first or radially compressed condition and received within annular groove 463 formed on knife carrier 420. Snap ring 180 is maintained in the radially compressed condition by an inner wall of pusher adapter 532. Notch 535 formed in the distal end of pusher adapter 532 is disposed distal of annular groove 463 and snap ring 180. In this manner, pusher assembly 530 may be advanced distally without causing the advancement of knife assembly 400.

In the initial position, pusher assembly 530 is prevented from inadvertent distal advancement relative to housing 120 through engagement of the plurality of paired detents 538a, 538b (FIG. 3) formed on distal portion 534 of pusher adapter 532 with openings 129 formed in outer cylindrical portion 122 of housing 120.

During a first or staple forming stroke of circular stapler 10, following approximation of anvil assembly 105 with respect to cartridge assembly 110 (e.g., via rotation of approximation knob 26), actuation of trigger 24 relative to handle 22 causes advancement of a drive assembly (e.g., 800) which operably engages pusher adapter 532 to cause the distal translation of pusher assembly 530. Distal translation of pusher adapter 532 advances pusher member 540 thereby causing pusher elements 546 to be advanced into and/or through staple receiving pockets 152 of staple cartridge 150 and to eject staples "S" from staple cartridge 150. Although not explicitly shown, the ejection of staples "S" from staple cartridge 150 causes advancement of staples "S" into staple-deforming pockets 602 of anvil head 600. Forming of staples "S" secures the tissue retained between staple cartridge 150 and anvil assembly 105.

Upon completion of the stapling stroke, pusher adapter 532 is refracted proximally relative to housing 120. Pusher adapter 532 is sufficiently retracted relative to knife carrier 420 and snap ring 180 such that snap ring 180 is aligned with notch 535 formed in the distal end of pusher adapter 532. Alignment of notch 535 with snap ring 180 allows snap ring 180 to move from the first or compressed condition to the uncompressed condition, i.e., snap ring 180 is able to decompress or radially expand.

During the second or cutting stroke of circular stapler 10, a second actuation of trigger 24 relative to handle 26 causes advancement of the drive member (e.g., 800) which operably engages pusher adapter 532 to cause the distal translation of pusher adapter 532. Distal translation of pusher adapter 532 causes ledge 536, defined by notch 535 formed in the distal end of pusher adapter 532, to engage an outer portion of snap ring 180 while an inner portion of snap ring 180 remains engaged with knife carrier 420. In particular, step 142a, formed within/adjacent groove 463 of knife carrier 420, engages snap ring 180 and prevents snap ring 180 from being radially compressed back into annular groove 463 during the second advancement of pusher adapter 532 during the second or tissue cutting stroke of circular stapler 10. Accordingly, step 462a of knife carrier 420 maintains snap ring 180 in the second or expanded condition such that snap ring 180 remains in contact with both pusher adapter 532 and knife carrier 420 to assure the simultaneous advancement of knife assembly 400 with the advancement of pusher adapter 532.

Continued advancement of pusher adapter 532 causes knife 440 to be received through longitudinal opening 151 of staple cartridge 150, thereby severing the tissue retained between staple cartridge 150 and anvil assembly 105, and thereby penetrating severable portion 628 of cutting ring 620. It is envisioned that pusher assembly 530 and knife assembly 400 may be configured such that retraction of the drive assembly causes the retraction of pusher adapter 532 and knife carrier 420 (see FIGS. 11-21, for example).

In addition to the reduced force requirements provided by the two stroke operation of circular stapler 10, the independent or decoupled staple forming and tissue cutting function of circular stapler 10 also permits the varying of the staple crimp height relative to the knife travel distance, the varying of the staple travel speed relative to the knife travel speed, and/or the addition of a dwell time between staple formation and tissue cutting. This configuration allows a clinician to optimize staple crimp heights to given conditions, such as, tissue thickness, tissue compliance and clamping force. This configuration may also allow for the monitoring of staple forming and knife cutting forces, to alert the clinician in case an abnormal force is detected. This configuration further allows force and other data to be monitored and used for data collection and research, which when analyzed, may lead to further optimization of operational parameters, such as staple crimp height, and dwell and travel speed. By independently controlling and optimizing these various parameters, improved hemostasis and anastomonic joint strength may result across a much broader range of tissue thicknesses, thereby allowing a clinician to have improved and customized control over the results. Further still, when the stapling and cutting functions are performed at the same time, the tissue being stapled may be displaced by the knife, thereby causing the staple legs to deflect and misalign with their intended anvil pockets, resulting in poor staple formation and possible leakage.

Figure 42:
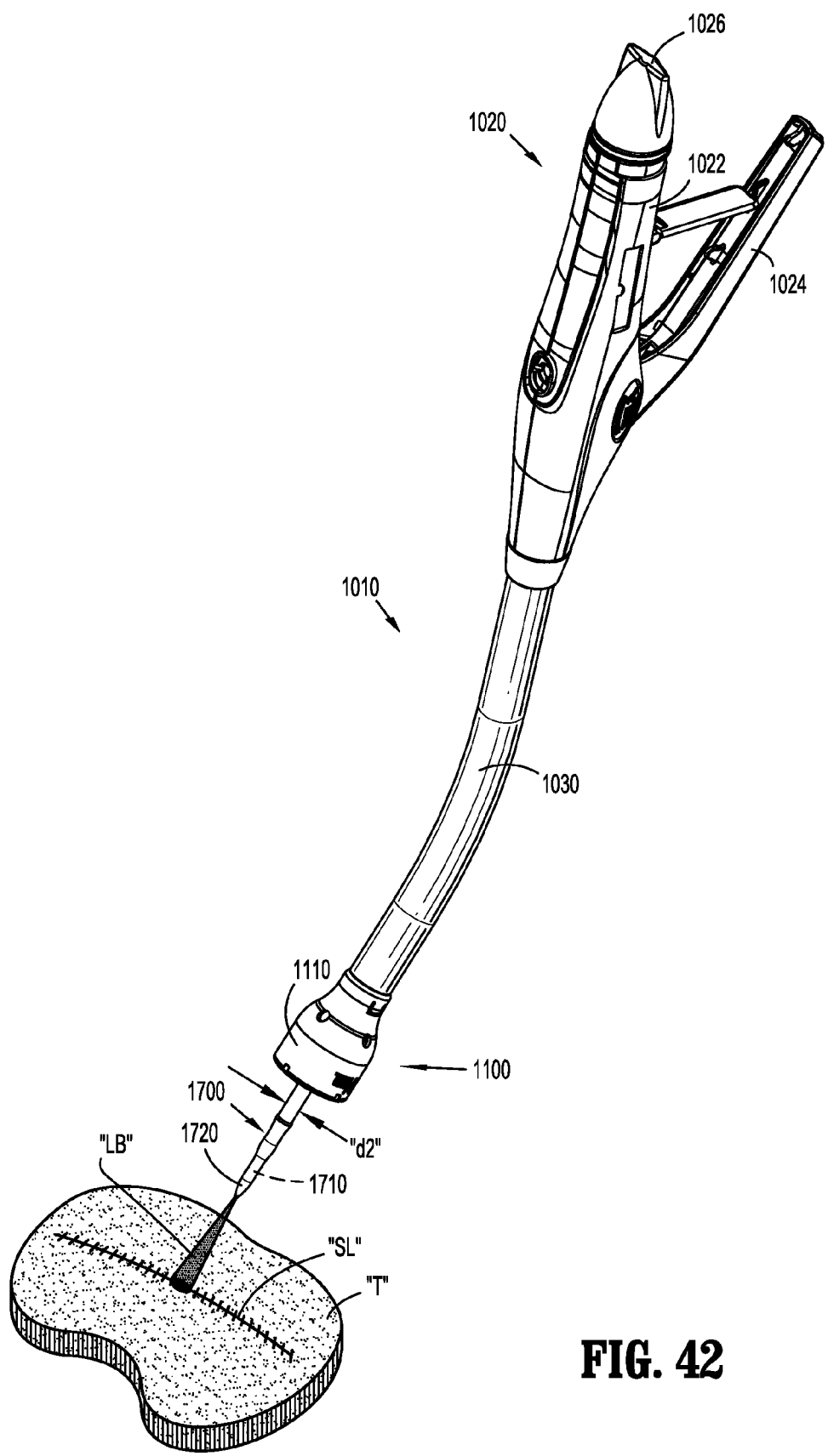
FIG. 42 is a perspective view of a surgical stapling instrument including a light according to embodiments of the present disclosure.
Figure 43:
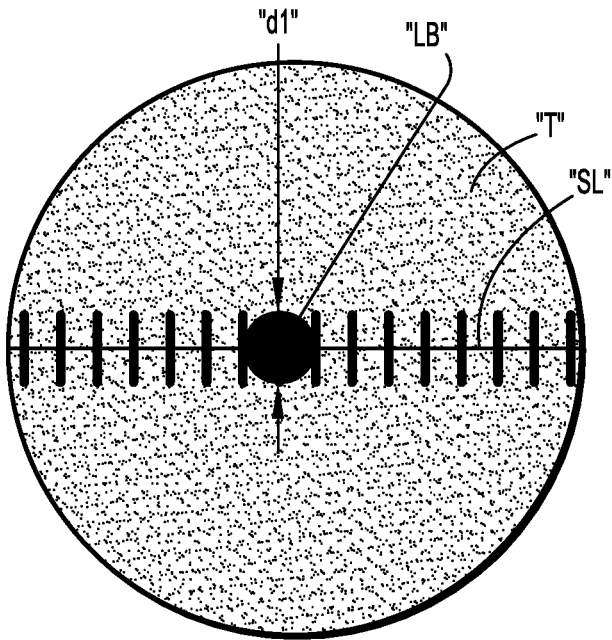
FIGS. 43 and 44 illustrate placement of a trocar of a surgical stapling instrument with respect to a linear staple line.
Figure 44:
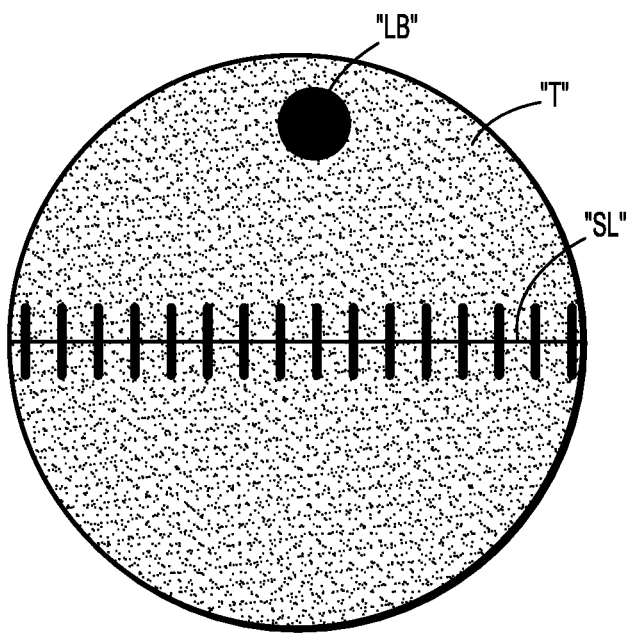

With reference to FIGS. 42-44, another embodiment of a surgical stapling instrument according to the present disclosure is shown in FIG. 42, and is referenced as circular stapler 1010. Circular stapler 1010 is similar to circular stapler 10 described above, and includes a handle assembly 1020, an elongated body portion 1030 extending distally from handle assembly 1020, a shell assembly 1100 mounted adjacent a distal end of elongated body portion 1030, a trocar 1700 extending distally from shell assembly 1100, and an anvil assembly (similar to anvil assembly 105 discussed above) including a retention rod, which selectively connects the anvil assembly 105 with trocar 1700. Handle assembly 1020 includes a fixed handle 1022 and a moveable handle or trigger 1024. Handle assembly 1020 also includes an approximation knob 1026 for moving trocar 1700 (and an attached anvil assembly) relative to a cartridge assembly 1110 of shell assembly 1100.

Additionally, trocar 1700 includes a light source 1710 which is configured to illuminate an area distally of trocar 1700. The light source can be an LED, laser or other light source. It is envisioned that light source 1710 is disposed within trocar 1700 (i.e., at least a portion of trocar 1700 is hollow) and that a distal tip 1720 of trocar 1710 is transparent or translucent to enable a light beam "LB" to shine through.

In disclosed embodiments, light source 1710 is configured to project the light beam "LB" onto a linear staple line "SL" in tissue "T" (FIGS. 42-44) to help ensure a desired placement of distal tip 1720 of trocar 1700 with respect to the linear staple line "SL." More particularly, prior to use of circular stapler 1010, a linear surgical stapling instrument (not explicitly shown) is often used to remove a section of a lumen by stapling and cutting the lumen proximally and distally of the section to be removed. The stapling of the lumen results in proximal and distal linear staple lines "SL." After the portion of the lumen is removed, circular stapler 1010 is used to join the proximal and distal portions of the lumen. Specifically, trocar 1700 of circular stapler 1010 is advanced through the proximal end of the lumen such that distal tip 1720 of trocar 1700 punctures or pierces the tissue. It is often advantageous to puncture the tissue on or as close as possible to the staple line "SL" (see FIG. 43). Such placement of distal tip 1720 of trocar 1700 can be challenging as it is often difficult for the surgeon to visualize exactly where distal tip 1720 of trocar 1700 will contact the tissue "T." As can be appreciated, when the surgeon cannot easily visualize exactly where distal tip 1720 of trocar 1700 will contact the tissue "T," the surgeon may place distal tip 1720 of trocar 1700 in a non-optimal location, such as a location or position spaced from the staple line "SL" (see FIG. 44).

As can be appreciated, light source 1710 of the present disclosure helps enable the surgeon to better visualize the target tissue, and thus helps ensure a desired placement of distal tip 1720 of trocar 1700 through the tissue (e.g., along the staple line "SL"). It is envisioned that light source 1710 includes a laser mounted on or associated with trocar 1700. Here, it is disclosed that the laser is configured to project a light beam "LB" (e.g., in a concentrated area) onto the tissue "T" aligned with the projected path of trocar 1710. Further, it is envisioned that the diameter "d1" (FIG. 43) of the light beam "LB" (e.g., the portion of the light beam "LB" on the tissue) is approximately the size of a diameter "d2" of a portion of trocar 1700 that is disposed distally of cartridge assembly 1110 when trocar 1700 is in a longitudinally advanced position (FIG. 42). The light beam "LB" is configured to be bright enough for a surgeon to visualize with or without the use of a laparoscopic camera. As such, the surgeon is able to slightly adjust the position of circular stapler 1010 while visualizing precisely where distal tip 1720 of trocar 1700 will puncture tissue (e.g., along the staple line "SL" as shown in FIG. 43).

The present disclosure also includes a method of performing an anastomosis. The method includes using circular stapler 1010, as described above, illuminating the target tissue "T" to show the projected path of trocar 1700, distally advancing trocar 1700 through the illuminated portion of the target tissue, engaging trocar 1700 with the retention rod of the anvil assembly, approximating the anvil assembly 105 with respect to cartridge assembly 1110, and firing fasteners from cartridge assembly 1110 toward the anvil assembly to join two sections of tissue.

It will be understood that various modifications may be made to the embodiments disclosed herein. For example, circular stapler 10, 1010 may include a mechanism for changing cartridge assembly 110, 1110 from two stroke operation to a single stroke operation. Additionally, light source 1710 may be disposed in mechanical cooperation with a different portion of circular stapler 1010 other than trocar 1700. For instance, light source 1710 may be coupled to shell assembly or cartridge assembly while still being configured to project a light beam "LB" onto target tissue "T." Therefore, the above description should not be construed as limiting, but merely as exemplifications of particular embodiments. Those skilled in the art will envision other modifications within the scope and spirit of the claims appended hereto.

The invention claimed is:

1. A circular stapler comprising:
a handle assembly;
an elongate body extending from the handle assembly and defining a longitudinal axis;
a cartridge assembly disposed adjacent a distal end of the elongate body, the cartridge assembly including a pusher assembly, the pusher assembly being movable to cause staples to be ejected from the cartridge assembly;
a trocar disposed in mechanical cooperation with the cartridge assembly and being longitudinally advanceable to puncture tissue, a distal tip of the trocar is one of transparent or translucent; and
a light source disposed in mechanical cooperation with the trocar, the light source configured to project a light beam distally of the trocar.

2. The circular stapler of claim 1, wherein the light source includes a laser.

3. The circular stapler of claim 2, wherein the laser is at least partially disposed within the trocar.

4. The circular stapler of claim 1, wherein the light source is disposed within the trocar.

5. The circular stapler of claim 1, wherein the light source is configured to project a light beam in a concentrated area directly in the path of travel of the trocar.

6. The circular stapler of claim 1, wherein the light source is configured to project a light beam that is approximately the size of a diameter of a portion of the trocar that is disposed distally of the cartridge assembly when the trocar is in a longitudinally advanced position.

7. The circular stapler of claim 1, where a distal tip of an axial center of the trocar is solid.

8. The circular stapler of claim 1, wherein a distal portion of the light source is longitudinally fixed from movement with respect to the trocar.

9. The circular stapler of claim 1, wherein the light source is longitudinally fixed from movement with respect to the trocar.

10. The circular stapler of claim 1, further including an anvil assembly disposed distally of the cartridge assembly and selectively engageable with the cartridge assembly, wherein an output of the light source is retained between the anvil assembly and the cartridge assembly.

11. A circular stapler comprising:
a handle assembly;
an elongate body extending from the handle assembly and defining a longitudinal axis;
a cartridge assembly disposed adjacent a distal end of the elongate body, the cartridge assembly including a pusher assembly, the pusher assembly being movable to cause staples to be ejected from the cartridge assembly;
a trocar disposed in mechanical cooperation with the cartridge assembly and being longitudinally advanceable to puncture tissue, a distal tip of an axial center of the trocar being solid; and a light source disposed in mechanical cooperation with the trocar, the light source configured to project a light beam distally of the trocar.

12. The circular stapler of claim 11, wherein an entirety of the light source is longitudinally fixed from movement with respect to the trocar.

13. The circular stapler of claim 11, wherein the distal tip of the trocar is one of transparent or translucent.

* * * * *

UNITED STATES PATENT AND TRADEMARK OFFICE
CERTIFICATE OF CORRECTION

| | | |
|---|---|---|
| PATENT NO. | : 9,757,133 B2 | Page 1 of 1 |
| APPLICATION NO. | : 14/326764 | |
| DATED | : September 12, 2017 | |
| INVENTOR(S) | : Latimer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 326 days.

Signed and Sealed this
Sixth Day of February, 2018

Joseph Matal
*Performing the Functions and Duties of the
Under Secretary of Commerce for Intellectual Property and
Director of the United States Patent and Trademark Office*